United States Patent [19]
Au-Yeung et al.

[11] Patent Number: 6,110,907
[45] Date of Patent: Aug. 29, 2000

[54] SYNTHESIS OF PLATINUM COMPLEXES AND USES THEREOF

[75] Inventors: Steve C. F. Au-Yeung, Shatin, The Hong Kong Special Administrative Region of the People's Republic of China; Yee Ping Ho, Tai Wai, The Hong Kong Special Administrative Region of the People's Republic of China; Lin Ge, Shatin, The Hong Kong Special Administrative Region of the People's Republic of China; Han Xiuwen, Dalian, China; Wang Xinning, Dalian, China; Lu Shiwei, Dalian, China; Jiang Tao, Dalian, China

[73] Assignees: Dalian Institute of Chemical Physics, Chinese Academy of Sciences, Dalian; The Chinese University of Hong Kong, Shatin, both of China

[21] Appl. No.: 09/069,562

[22] Filed: Apr. 29, 1998

[51] Int. Cl.[7] ............................ A61K 31/555; C07F 15/00
[52] U.S. Cl. ............................................. 514/185; 549/206
[58] Field of Search ..................................... 549/348, 349, 549/459, 206; 514/450, 468, 185

[56] References Cited

U.S. PATENT DOCUMENTS

| 4,140,707 | 2/1979 | Cleare et al. | 260/429 R |
| 4,675,336 | 6/1987 | Bitha et al. | 514/492 |

FOREIGN PATENT DOCUMENTS

WO/9216539  10/1992  WIPO .

OTHER PUBLICATIONS

Zou et al CA126:194919, 1997.
Zou, Juan, et al., "Synthesis Antitumor, Activity and Acute Toxicity of Diammine/Diamino–Cylohexane Platinum (II) Complexes With Oxygen–Ligating Leaving Group" *Journal of Inorganic Biochemistry* (1997) vol. 65: No. 2, pp. 145–149.
"Chemical Abstracts" (Nov. 15, 1997) vol. 126:194919v No. 15, p. 25.
The International Search Report of PCT/CN98/00069 corresponding to the above–identified subject application, dated Jul. 2, 1998, and a copy of the filed PCT International .

*Primary Examiner*—Amelia Owens
*Attorney, Agent, or Firm*—Albert Wai-Kit Chan; Paul Teng; Cooper & Dunham LLP

[57] ABSTRACT

This invention provides novel antitumor demethylcantharidin platinum complexes. This invention also provides a composition comprising at least one of said demethylcantharidin platinum complexes and a suitable carrier. This invention provides a pharmaceutical composition comprising effective amount of at least one of the said demethylcantharidin platinum complexes and a pharmaceutically acceptable carrier. This invention provides a method of inhibiting the growth of tumorous cells comprising contacting the cells with an amount of said demethylcantharidin platinum complex effective to inhibit the growth of said tumorous cells. This invention provides a method of inhibiting the growth of tumorous cells in a subject comprising administering to the subject with an amount of the said demethylcantharidin platinum complexes effective to inhibit the growth of said tumorous cells in the subject. Finally, this invention provides methods for producing said demethylcantharidin platinum complexes.

16 Claims, 9 Drawing Sheets

FIG. 1A
Novel Compounds
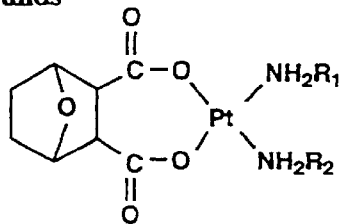
Compounds A, B, C, D
Other series of compounds under development:
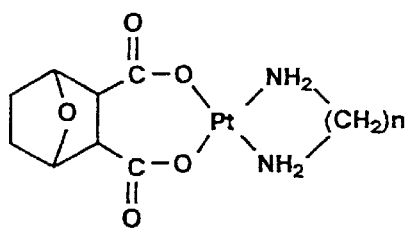
FIG. 1B
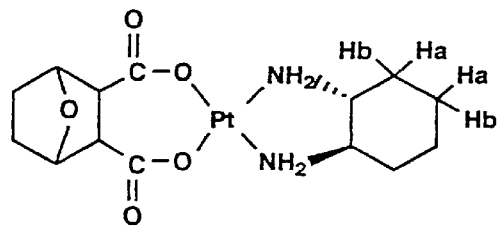
FIG. 1C
Cisplatin
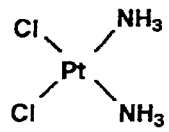
FIG. 1D
Carboplatin
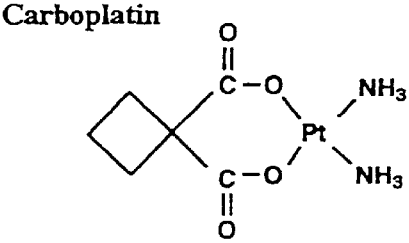
FIG. 1E
Cantharidin
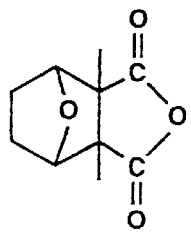
FIG. 1F
Demethyl cantharidin
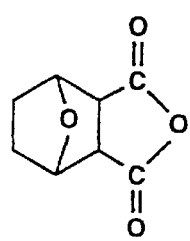
FIG. 1G

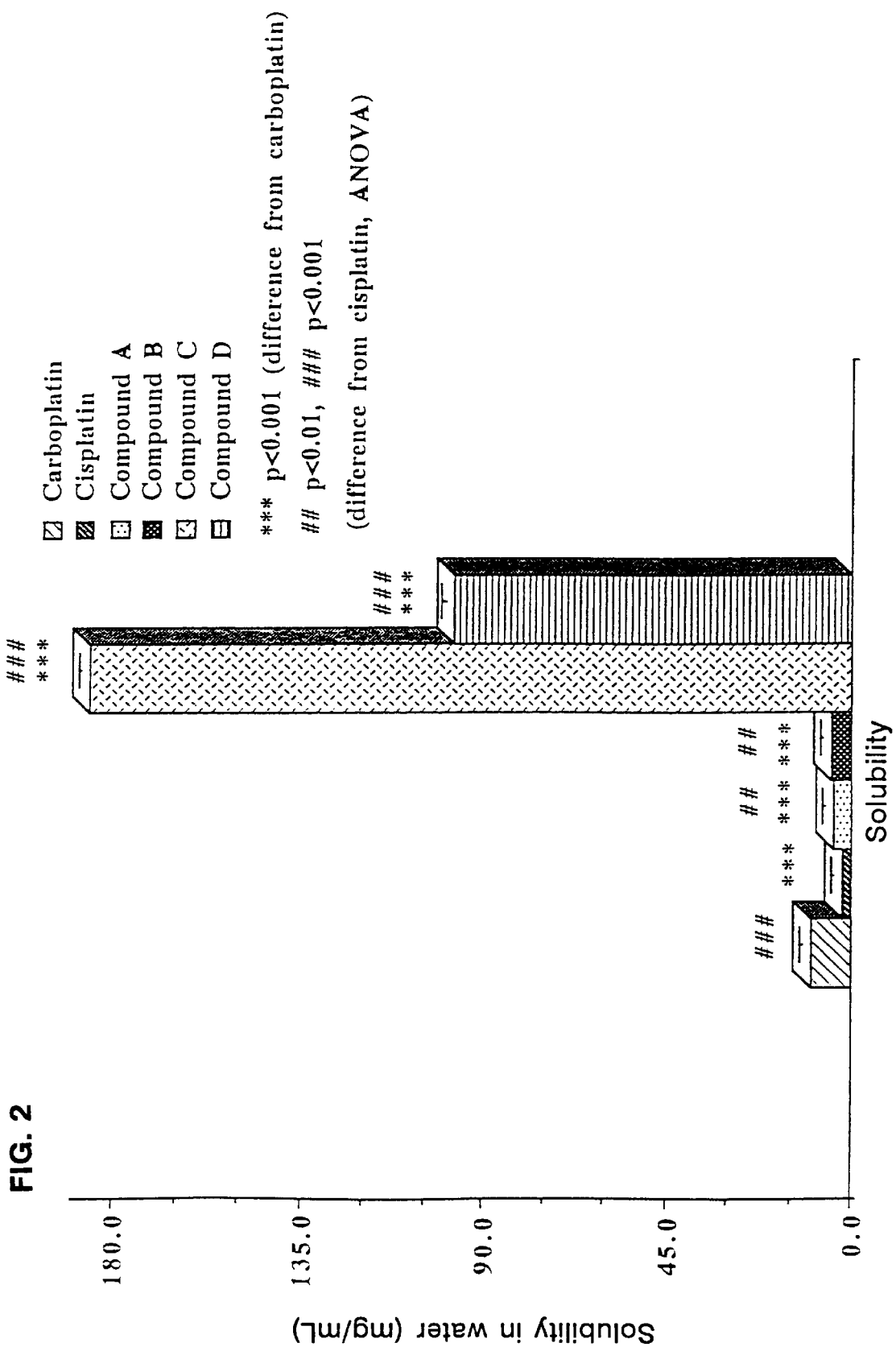

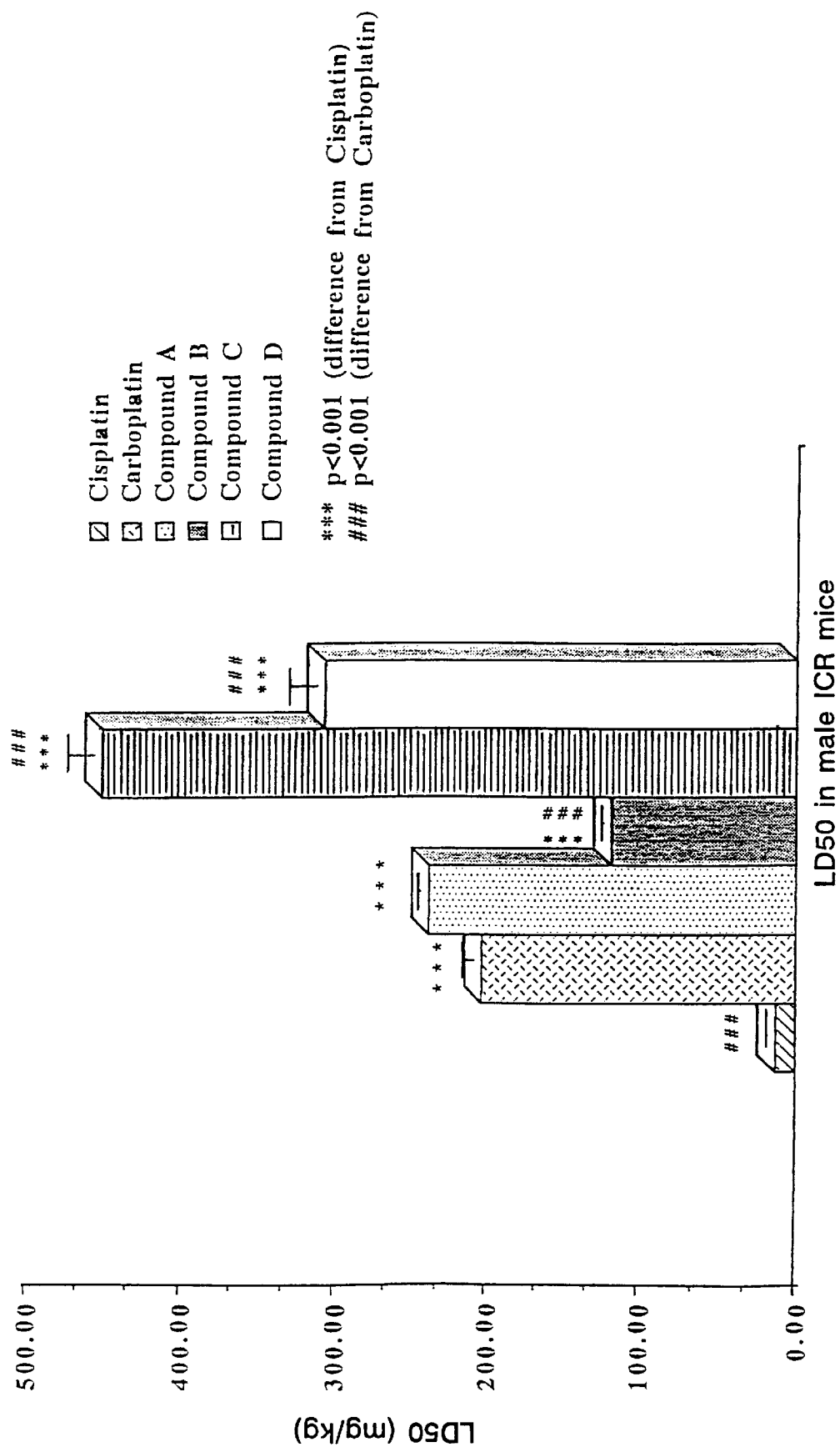

SYNTHESIS OF PLATINUM COMPLEXES AND USES THEREOF

BACKGROUND OF THE INVENTION

There are currently only two platinum (Pt)-based drugs which are marketed and clinically used as antitumor drugs: cisplatin and carboplatin (FIG. 1). Common problems associated with these drugs include toxic side effects and low solubility in aqueous media. This invention provides method to synthesize novel Pt compounds with superior biological and physicochemical properties.

There are a large number of systems being pursued internationally, all of which are based on the modification of one and/or both of the ligand types coordinated to Pt. The principal design philosophy provided by this invention was to utilize active components in traditional Chinese medicine (TCM) with known therapeutic value, as the ligand choice (leaving group) for the synthesis of platinum based antitumor drugs.

Cantharidin is the active principle of "blister beetles" and has demonstrated high affinity and specificity towards the liver. In TCM, cantharidin is mainly used for treatment of liver, lung, intestinal and digestive tract tumors. However, severe side effects due to cantharidin has been documented, including nausea and vomiting, dysphagia, hematemesis, gross hematuria and dysuria.

Demethyl cantharidin (FIG. 1) was selected as a ligand for the synthesis of a novel series of Pt complexes because:

1. It is structurally similar to cantharidin, therefore should present similar structure-activity relationship (SAR). The novel Pt complexes may be specifically targeted towards liver and gastrointestinal tract tumors.
2. It has lower toxicity ($LD_{50}$ 4 mg/kg) than cantharidin ($LD_{50}$ 1 mg/kg) and its corresponding dicarboxylic acid is also less toxic ($LD_{50}$ 14 mg/kg).
3. The structures of the compounds provided by this disclosure resemble that of carboplatin, an established second generation platinum antitumor drug currently in clinical use as an effective antitumor agent.

SUMMARY OF THE INVENTION

This invention provides a demethylcantharidin platinum complex having the following structure:

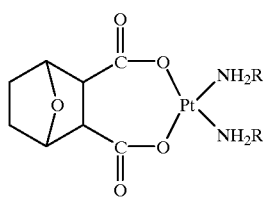

Structure I wherein R=H, C1–C10 or ring size C3–C6.

This invention also provides a demethylcantharidin platinum complex having the following structure:

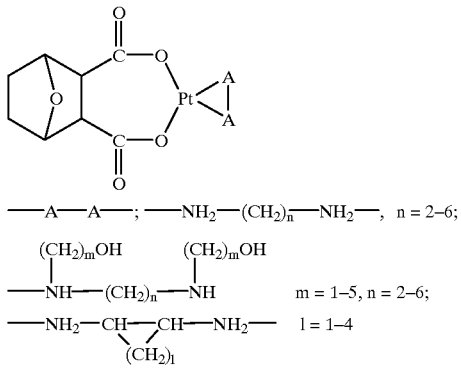

Structure II

This invention also provides a composition comprising at least one of the above demethylcantharidin platinum complexes and a suitable carrier.

This invention provides a pharmaceutical composition comprising effective amount of at least one of the above demethylcantharidin platinum complexes and a pharmaceutically acceptable carrier.

This invention provides a method of inhibiting the growth of tumorous cells comprising contacting the cells with an amount of the above demethylcantharidin platinum complex effective to inhibit the growth of said tumorous cells.

This invention provides a method of inhibiting the growth of tumorous cells in a subject comprising administering to the subject with an amount of the above demethylcantharidin platinum complexes effective to inhibit the growth of said tumorous cells in the subject.

Finally, this invention provides methods for producing the above demethylcantharidin platinum complexes.

BRIEF DESCRIPTION OF THE FIGURES

FIG. 1. 1A: Generic structure for compounds A, B, C and D; 1B, 1C other series of compounds under development; 1D Cisplatin; 1E Carboplatin; 1F Cantharidin and 1G Demethylcantharidin.

FIG. 2. Solubility of Carboplatin, Cisplatin, Compounds A, B, C and D. ***$p<0.001$ (difference from carboplatin) ## $p<0.01$, ###$p<0.001$ (difference from cisplatin, ANOVA)

FIG. 3. LD50 (mg/Kg) of Cisplatin, Carboplatin, Compounds A, B, C and D. ***$p<0.001$ (difference from cisplatin). ###$p<0.001$ (difference from carboplatin)

DETAILED DESCRIPTION OF THE INVENTION

Figure 4:
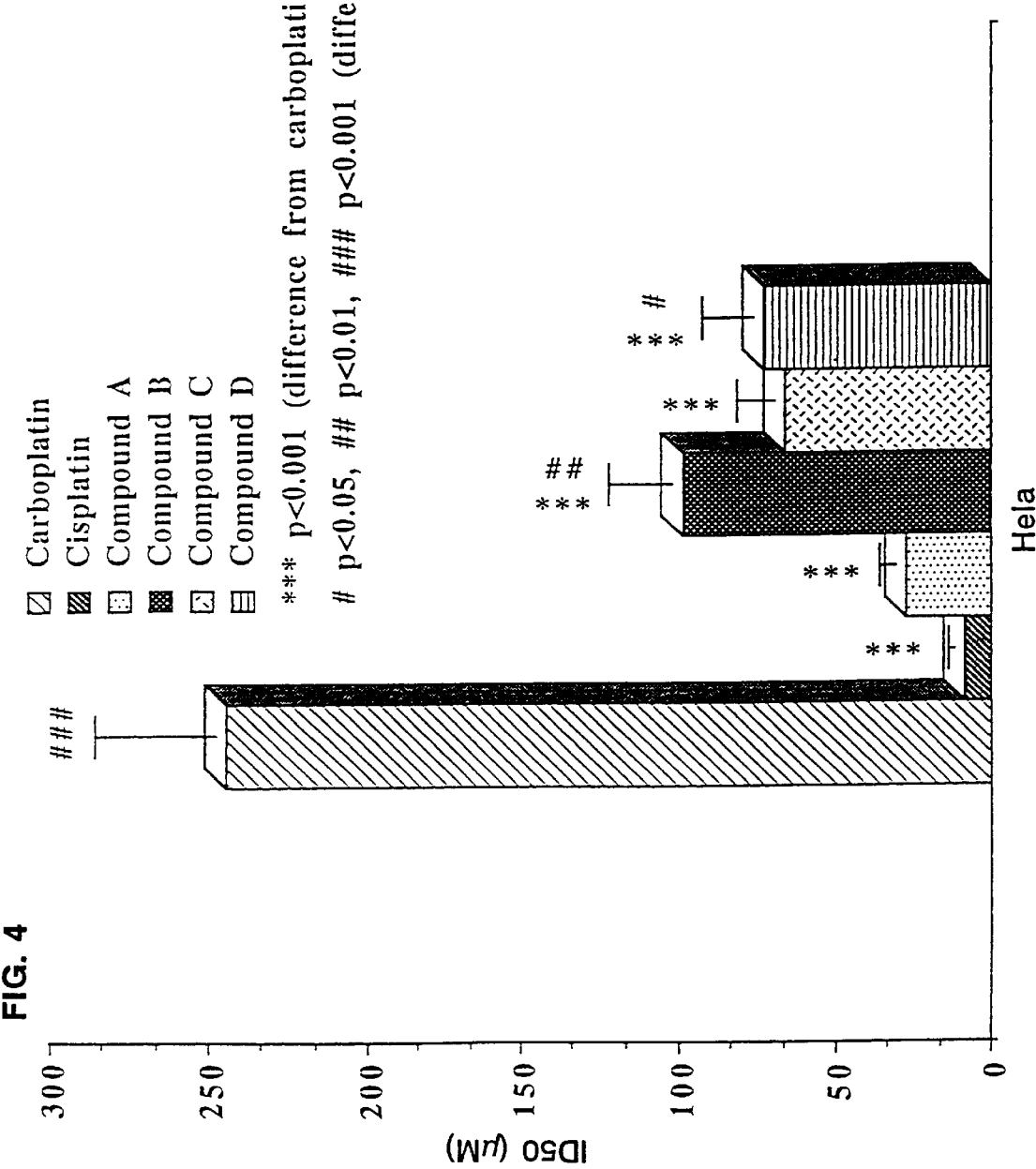
FIG. 4. ID50 (uM) of Carboplatin, Cisplatin, Compounds A, B, C and D in Hela cells. ***$p<0.001$ (difference from carboplatin, n=16). ## $p<0.05$, ###$p<0.001$ (difference from cisplatin)

This invention provides a type of new antitumor drug, demethylcantharidin platinum complexes, with structure of type either (I) or (II):

Structure I

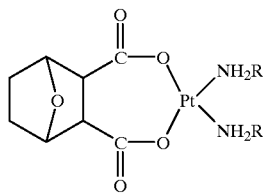

wherein R=H, C1–C10 or ring size C3–C6;

Structure II

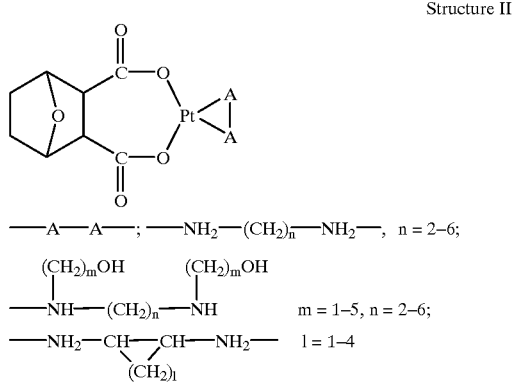

This invention also provides platinum complexes as shown in the above Structure I, wherein R=H, —CH$_3$, —C$_2$H$_5$, —C$_3$H$_7$, CH(CH$_3$)$_2$, or cyclopropyl.

This invention also provides a composition comprising the above-described demethylcantharidin platinum complexes and a suitable carrier. Suitable carriers are well-known in the art. For example, the carrier may be an aqueous solvent.

This invention further provides a pharmaceutical composition comprising effective amount of the above-described demethylcantharidin platinum complexes and a pharmaceutically acceptable carrier.

Pharmaceutically acceptable carriers are well-known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

This invention also provides the above-described pharmaceutical composition used to inhibit growth of tumor cells. Such tumor may be derived from lung, liver or colon. In addition, the tumor can be leukemia, lymphoma, nasopharyngeal carcinoma or cervical tumor.

The novel compound provided by the disclosure may also be used to inhibit growth of testicular, ovarian, stomach, head and neck, and colorectal tumor. Once the compound is synthesized, the compound can be tested by known procedure for its antitumor activity.

This invention also provides a method of inhibiting the growth of tumorous cells comprising contacting the cells with an amount of the above-described demethylcantharidin platinum complexes effective to inhibit the growth of said tumorous cells.

This invention provides a method of inhibiting the growth of tumorous cells in a subject comprising administering to the subject with an amount of the above-described demethylcantharidin platinum complex effective to inhibit the growth of said tumorous cells in the subject.

As used in this invention the tumorous cells may be derived from lung, liver or colon. The tumorous cells can be leukemia cells, lymphoma cells, naso-pharyngeal carcinoma cells or cervical tumor cells. The novel compound provided by the disclosure may also be used to inhibit growth of testicular, ovarian, stomach, head and neck, and colorectal tumor.

For the purposes of this invention, "administering" means any of the standard methods of administering known to those skilled in the art. Examples include, but are not limited to, intravenous, intraperitoneal or intramuscular administration.

An "effective amount" is any amount effective to inhibit the growth of said tumorous cells in the subject. Methods of determining an "effective amount" are well known to those skilled in the art and depend upon a number of factors including, but not limited to: the type of subject involved, the size of the blood sample contacted and the detectable marker used. In one embodiment of this invention, the detectable marker is a radioisotope, enzyme, dye or biotin.

In an embodiment, the subject is an animal. In another embodiment, the subject is a human.

One method to synthesize the demethylcantharidin platinum complex is as follows:

(1) Preparation of Demethylcantharidin Ligand B.

Furan and maleic anhydride are dissolved in tetrahydrofuran (THF) to obtain intermediate A, which was dissolved in ethylacetate and Pd-C catalyst added to obtain Ligand B.

STRUCTURES OF LIGAND A & B

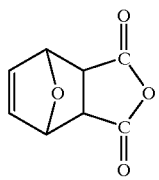

Ligand A

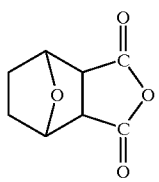

Ligand B (2) Preparation of Pt (II) Nitrate Complex.

$K_2PtCl_4$ was converted to the iodide $K_2PtI_4$, followed by addition of amine ligand (A) or two equivalents (2A). Silver nitrate is then added to $PtA2I_2$ to produce $A_2Pt(NO_3)_2$.

(3) Synthesis of Demethylcantharidin Pt Complex.

Ligand B was added to the prepared $A_2Pt(NO_3)_2$ followed by NaOH to give the demethylcantharidin platinum complex.

In an embodiment, the Pt (II) nitrate complex is obtained directly from 2A, $K_2PtCl_4$ and $AgNO_3$.

Pharmaceutically acceptable carriers are well-known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

This invention will be better understood from the Experimental Detail which follow. However, one skilled in the art will readily appreciate that the specific methods and results discussed are merely illustrative of the invention as described more fully in the claims which follow thereafter.

First Series of Experiment

This invention describes the synthesis of a novel series of drugs based on demethylcantharidin platinum complexes. The discovery of antitumor properties of cisplatin opened up the use of transition metal complexes in tumor chemotherapy. Thus far, over 3000 platinum complexes have been synthesized, amongst which 1000 have antitumor activity and more than 10 are undergoing clinical trials.

Although cisplatin has superior antitumor activity, poor solubility and severe toxicity seriously restrict its long term use and in large doses. Second generation platinum antitumor drugs, for example, carboplatin has better solubility than cisplatin and with a higher therapeutic index. The side effects are significantly lower but carboplatin strongly irritates the gastrointestinal tract and it has narrow antitumor spectrum, therefore its use is restricted.

For this reason, synthesis of new platinum compounds with higher potency, lower toxicity, broad spectrum activity, better aqueous solubility has become the major direction in this research area.

Cantharidin, extracted from "blister beetles" is a substance of lethal toxicity. Blister beetles have been used as a traditional Chinese medicine (TCM) and has been reported since ancient times as an antitumor agent. During the last few decades, interest in the study of cantharidin, its pharmacology and clinical use has dramatically intensified.

Currently, the method of isolation of cantharidin from powdered beetles is to use solvents such as acetone and chloroform. But there are no reports of cantharidin being used as a coordination ligand in the synthesis of platinum-complex antitumor drugs.

This invention is to use demethylcantharidin as coordination ligand to synthesize novel platinum complexes with less toxicity, good aqueous solubility and with broader spectrum of antitumor activity. These complexes have potential to become new antitumor drugs. The method of synthesis of this type of platinum complex is also described.

One example within this invention is choosing the less toxic demethylcantharidin as coordination ligand in the synthesis of novel platinum complexes. The structures of the complexes are given in formula (I) or (II).

STRUCTURES I & II

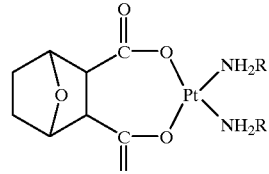

Structure I

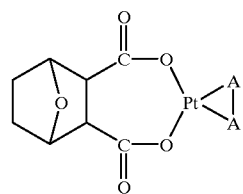

Structure II wherein R=H, $C_1$–$C_{10}$; ring size $C_{3-6}$

—A—A—: —$NH_2$—$(CH_2)_n$—$NH_2$—, n = 2–6;

$\begin{matrix}(CH_2)_mOH & (CH_2)_mOH \\ | & | \\ \text{—NH—} & (CH_2)_n\text{—NH—}\end{matrix}$   m = 1–5, n = 2–6;

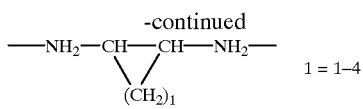

$1 = 1–4$

In Structure I, when R is H, $CH_3C_2H_5$, $C_3H_7$, isopropyl or cyclopropyl, the complexes show better antitumor activity.

The platinum complex as shown in Structure II, where n=2 to 3; m=2; l=4, becomes trans 1,2-diaminocyclohexyl (DACH), show better antitumor activity.

The method of synthesis of demethylcantharidin platinum complexes has the following steps:

1. Preparation of Demethylcantharidin Ligand B.

Furan and maleic anhydride with tetrahydrofuran (THF) as solvent were reacted and intermediate A was obtained. Ligand A was dissolved in ethyl acetate and Pd-C catalyst was added. The reaction mixture was refluxed and hydrogen gas was added to synthesize Ligand B (Scheme 1).

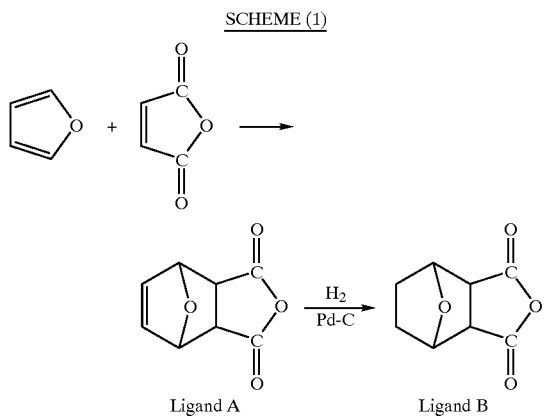

SCHEME (1)

Ligand A     Ligand B

2. Synthesis of Pt (II) Nitrate Derivative.

$K_2PtCl_4$ was converted to the iodide $K_2PtI_4$, followed by addition of amine ligand (A) or two equivalents (2A). Silver nitrate is then added to $PtA_2I_2$ to produce $A_2Pt(NO_3)_2$. Two equivalents of the amine ligand (2A) can also be added directly to $K_2PtCl_{41}$ followed by addition of $AgNO_3$ to give $A_2Pt(NO_3)_2$ (Scheme 2).

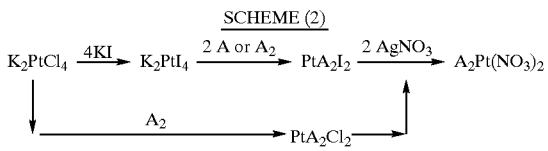

SCHEME (2)

3. Synthesis of Demethylcantharidin Pt Complex.

To the Ligand B, synthesized from Scheme 1, was added the prepared $A_2Pt(NO_3)_2$ followed by NaOH to give the demethylcantharidin platinum complex (Scheme 3).

SCHEME (3)

In Scheme 3, $A=NH_2R$. Products were identified by IR and NMR (500 MHz).

EXAMPLE 1

Preparation of Demethylcantharidin Ligand B

Furan (5.4 ml, 0.073 mol) and maleic anhydride (6 g, 0.061 mol) were placed into a dry beaker with THF (8 ml) and contents stirred at room temperature for 60 minutes. Solvent was removed in vacuo, and the crude material recrystallized from ethyl acetate. White crystals of intermediate A were obtained (9.1 g, 88.4% yield). Intermediate A (2 g, 0.012 mol) was dissolved in ethyl acetate (30 ml) and Pd-C catalyst (5% Pd, 0.2 g) was added. The reaction mixture was stirred, refluxed and hydrogen gas bubbled into the reaction flask at atmospheric pressure for 6 hours. Solvent was removed in vacuo and Ligand B was obtained (98% yield), melting point: 116.9~117.3° C.

IR (KBr, $cm^{-1}$): 1843, 1784 (C=O), 1237, 1099, 890 (C—O—C). $^1$H NMR ($CDCl_3$, δ/ppm): 2.99 (s, 2H, H-5 & H-6), 3.63 (s, 2H, H-2 & H-3), 4.92 (s, 2H, H-1 & H-4).

EXAMPLE 2

Synthesis of Compound Having Structure I, (R=H) ... (1)

$K_2PtCl4$ (0.845 g, 1.93 mmol) was dissolved in water (15 ml), heated to 80° C., and KI (1.92 g, 11.6 mmol) was added into the solution and mixture was allowed to react in the dark for 15 minutes at 80° C. The reaction system was cooled to 40° C. and $NH_3$ (aq, 30%) was added dropwise, keeping the pH <7. A dark yellow precipitate was formed and $NH_3$ (aq, 30%) was continuously added until pH remained at 8. The reaction mixture was stirred at 40° C. for 2 hrs, then filtered and precipitate washed with water (5 ml), ethanol (5 ml) and diethyl ether (5 ml) to produce $(NH_3)_2PtI_2$ (0.88 g, 95% yield). $(NH_3)_2PtI_2$ (0.483 g, 1 mmol) and $AgNO_3$ (0.34 g, 2 mmol) were placed into a beaker with water (25 ml). The reaction mixture was stirred in the dark at RT for 16 hrs, filtered and solid AgI removed.

Ligand B (0.168 g, 1 mmol) and NaOH (0.08 g, 2 mmol) was added into the filtrate containing $(NH_3)_2Pt(NO_3)_2$ and mixture was allowed to stir at RT for 8 hrs. A white solid precipitate was formed, filtered and washed with ice water (5 ml), ethanol (5 ml) and diethyl ether (5 ml) to give product (1) (0.28 g, 58%).

IR (KBr, cm$^{-1}$): 3250, 3207 (N—H), 1652 (C=O), 1384 (COO$^-$), 1258, 1222, 1034, 989, 878 (C—O—C), 418 (Pt-N).

$^1$H NMR (D$_2$O, δ/ppm): 1.72 (s, 2H, H-2 & H-3), 4.02 (s, 2H, H-5 & H-6), 4.92 (s, 2H, H-1 & H-4).

EXAMPLE 3

Synthesis of Compound Having Structure I, (R=CH$_3$) . . . (2)

K$_2$PtCl$_4$ (0.9959 g, 2.40 mmol) was dissolved in water (10 ml). The solution was heated to 80° C., then KI (1.9104 g, 11.5 mmol) was added and mixture allowed to react for 15 mins. The dark mixture was cooled to 50° C. and 35% CH$_3$NH$_2$ (0.425 g, 4.8 mmol) was added dropwise and a yellow ppt was formed immediately. The reaction mixture was kept at 60° C. for 3–4 hr, cooled to RT, filtered and ppt washed with water (5 ml) and ethanol (5 ml) before being air dried. Yield: 1.13 g (92%).

AgNO$_3$ (0.6769 g, 3.98 mmol) and Pt(CH$_3$NH$_2$)$_2$I$_2$ (1.1073 g, 1.99 mmol) were placed into the reaction flask with water (10 ml). The mixture was stirred in the dark for 24 hr, filtered and solid AgI removed. Ligand B (0.3343 g, 1.99 mmol) and NaOH (0.1592 g, 3.98 mmol) were added into the solution of Pt(MeNH$_2$)$_2$(NO$_3$)$_2$ and mixture was allowed to stir at RT for 1 day. Water was removed in vacuo and after washing with ice water (5 ml), yield of product at this stage was 0.17 g. The water wash layer volume was reduced down to 1~2 ml and the contents kept in the dessicator with a beaker of P$_2$O$_5$. Two days later, a light yellow crystalline product was formed and washed with a small amount of ice water. The yield of product obtained was 0.18 g. Total yield of product was 0.35 g, 40%.

IR (KBr, cm$^{-1}$): 3247, 3152, 3099 (N—H), 1651, 1626 (C=O), 1371 (COO$^-$), 1248, 1190, 1098, 991 (C—O—C), 420 (Pt-N). $^1$H NMR (D$_2$O, δ/ppm): 1.65 (s, 4H, H-2 & H-3), 2.21 (s, 6H, 2-CH$_3$), 3.86 (s, 2H, H-5 & H-6), 4.85 (s, 2H, H-1 & H-4). $^{13}$C NMR (D$_2$O, δ/ppm): 31.05 (C-2 & C-3), 35.57 (CH$_3$), 59.58; (C-5 & C-6), 81.59 (C-1 & C-4), 184.04 (C=O).

EXAMPLE 4

Synthesis of Compound Having Structure I, (R=C$_2$H$_5$) . . . (3)

K$_2$PtCl$_4$ (1.1025 g, 2.66 mmol) was dissolved in water (10 ml). KI (2.2961 g, 13.8 mmol) was added to the solution. The mixture was stirred at 80° C. for 15 mins, followed by cooling to 50° C., before 70% C.$_2$H$_5$NH$_2$ (0.342 g, 5.32 mmol) was added, pH~8. The reaction mixture was stirred at 60° C. for 3–4 hr, then filtered and ppt washed with water (5 ml) and ethanol (5 ml). Yield obtained was 1.3 g (93%).

AgNO$_3$ (0.7644 g, 4.5 mmol) and Pt(EtNH$_2$)$_2$I$_2$ (1.2118 g, 2.25 mmol) were placed in the reaction flask with water (10 ml). The mixture was stirred in the dark at RT for 24 hr, filtered and AgI removed. Ligand B (0.360 g, 2.25 mmol) and NaOH (0.180 g, 4.5 mmol) was added to the filtrate and the mixture allowed to stir at RT for 2 days. Water was removed in vacuo and the solid was washed with ice water (5 ml). Product yield was 0.4 g. The water wash layer was collected and the volume reduced to 1 ml. This sample was then kept in the dessicator with a beaker of P$_2$O$_5$. A light yellow crystalline product was formed which was filtered and washed with water (5 ml). Product obtained was 0.06 g. Total product yield was 0.46 g (45%).

IR (KBr, cm$^{-1}$): 3249, 3195, 3127 (N—H), 1638, 1594 (C=O), 1389 (COO$^-$), 1265, 1081, 933 (C—O—C), 410 (Pt-N). $^1$H NMR (D$_2$O, δ/ppm): 1.13 (t, 6H, H-8 & H-10), 1.62 (s, 4H, H-2 & H-3), 2.63 (q, 4H, H-7 & H-9), 3.64 (s, 2H, H-5 & H-6), 4.65 (s, 2H, H-1 & H-4). $^{13}$C NMR (D$_2$O, δ/ppm): 17.86 (C-8 & C-10), 30.31 (C-2 & C-3) 44.32 (C-7 & C-9), 59.33 (C-5 & C-6), 81.34 (C-1 & C-4), 183.93 (C=O).

EXAMPLE 5

Synthesis of Compound Having Structure I, (R=C$_3$H$_7$) . . . (4)

K$_2$PtCl$_4$ (0.8458 g, 2.038 mmol) was dissolved in water (10 ml) and heated to 80° C. KI (2.0298 g, 12.228 mmol) was added and mixture stirred for 15 mins. The resultant black solution was cooled to 50° C. and n-propylamine (0.2405 g, 4.076 mmol dissolved in 1 ml H$_2$O) was added to give a yellow ppt. The reaction was allowed to stir at 60° C. for a further 3–4 hr before being cooled. The mixture was then filtered, washed with water (5 ml) and air dried. Yield of product was 0.9342 g, 80%.

AgNO$_3$ (0.319 g, 1.88 mmol) and Pt(CH$_3$CH$_2$CH$_2$NH$_2$)$_2$I$_2$ (0.532 g, 0.94 mmol), and water (10 ml) were added together and mixture stirred in the dark for 24 hr. The mixture was filtered and a filtrate containing Pt(nPrNH$_2$)$_2$(NO$_3$)$_2$ was obtained. Ligand B (0.1576 g, 0.94 mmol) and NaOH (0.075 g, 1.877 mmol) were added to the filtrate and the reaction mixture stirred at RT for 16 hr whereby a white ppt was formed. The water was removed in vacuo and the solid washed with ice water (5 ml) ethanol (5 ml) and diethyl ether (5 ml). Yield of the final product was 0.209 g (45%).

IR (KBr, cm$^{-1}$): 3196, 3134 (N—H), 1664, 1650 (C=O), 1474 (CH2), 1383 (COO—), 1370 (CH3), 1265, 994 (C—O—C). $^1$H NMR (D$_2$O, δ/ppm): 0.94 (t, 6H, H-9 & H-9'), 1.70 (m, 4H, H-8 & H-8'), 1.75 (q, 4H, H-2 & H-3), 2.76 (t, 4H, H-7 & H-7'), 3.77 (s, 2H, H-5 & H-6), 4.94 (d, 2H, H-1 & H-4). $^{13}$C NMR (D$_2$O, δ/ppm): 13.18 (C-9 & C-9'), 26.26 (C-8 & C-8'), 30.27 (C-2 & C-3), 51.28 (C-7 & C-7'), 59.29 (C-5 & C-6), 81.30 (C-1 & C-4), 183.92 (C=O).

EXAMPLE 6

Synthesis of Compound Having Structure I, (R=CH(CH$_3$)$_2$) . . . (5)

H$_2$PtCl$_6$.5H$_2$O (1 g, 2 mmol) was dissolved in water (15 ml), heated to 60° C. and a solution of N$_2$H$_4$.2HCl (0.107 g in 5 ml water, 1 mmol) was added dropwise. Ten minutes later, KCl (0.328 g, 4.4 mmol) was added and the reaction mixture was stirred for 30 minutes. KI (1.59 g, 9.6 mmol) was added into the solution, heated to 80° C. The mixture was allowed to react in the dark for 15 minutes, followed by cooling to 50° C., and i-PrNH$_2$ (0.826 g in 2 ml water, 14 mmol) was added dropwise. A dark yellow precipitate was formed and the mixture was stirred at 60° C. for 4 h, then kept at 0° C. for 4 h. The mixture was filtered and the ppt washed with water (5 ml), ethanol (5 ml) and diethyl ether (5 ml), then air-dried.

Pt (i-PrNH$_2$)0.2I$_2$ (0.5616 g, 0.99 mmol) and AgNO$_3$ (0.3368 g, 1.98 mmol) were placed in a beaker with 25 ml water. The mixture was stirred in the dark for 16 h, filtered and the solid AgI removed. Ligand B (0.1663 g, 0.99 mmol) and NaOH (1.98 mmol) were added into the solution and stirred at RT for 8 h. The mixture was distilled in vacuo and a white solid was obtained, which was washed with ice-water (5 ml), ethanol (5 ml) and diethyl ether (5 ml). The yield of product was 0.19 g, 39%.

IR (KBr, cm$^{-1}$): 3218, 3152 (N—H), 1652, 1604 (C=O), 1383 (COO$^-$), 1365, (CH$_3$), 1273, 941 (C—C—C). $^1$H NMR (D$_2$O, δ/ppm): 1.35 (d, 12H, 4—CH$_3$), 1.75 (s, 2H, H-2, H-3), 2.90 (m, 2H, CH, H-7 & H-7'), 3.91 (s, 2H, H-5, H-6), 4.95 (s, 2H, H-1, H-4).

$^{13}$CNMR (D$_2$O, δ/ppm): 24.95 (CH$_3$), 25.17 (CH$_3$), 30.13 (C-2, C-3), 51.11 (C-7 & C-7'), 59.06 (C-5, C-6), 81.48 (C-1, C-4), 183.63 (C=O).

EXAMPLE 7

Synthesis of Compound Having Structure I, (R= cyclopropyl) . . . (6)

K$_2$PtCl$_4$ (0.4420 g, 1.0651 mmol) was dissolved in water (10 ml) and heated to 80° C. KI (1.0608 g, 6.3904 mmol) was added and mixture stirred for 15 mins. The resultant black solution was cooled to 50° C. and cyclopropylamine (CPA) (0.1214 g, 2.13 mmol dissolved in 1 ml H$_2$O) was added to give a yellow ppt. The reaction was allowed to stir at 60° C. for a further 3–4 hr before being cooled. The mixture was then filtered, washed with water (5 ml) and air dried. Yield of product was 0.57 g, 95%.

AgNO$_3$ (0.3011 g, 1.76 mmol) and Pt(CPA)$_2$I$_2$ (0.4987 g, 0.88 mmol), and water (10 ml) were added together and mixture stirred in the dark for 18 hr. The mixture was filtered to remove AgI. Ligand B (0.147 g, 0.88 mmol) and NaOH (0.075 g, 1.76 mmol) were added to the filtrate and the reaction mixture stirred at RT for 16 hr whereby a white ppt was formed. The water was removed in vacuo and the solid washed with ice water (5 ml), ethanol (5 ml) and diethyl ether (5 ml). Yield of the final product was 0.15 g (35%).

IR (KBr, cm$^{-1}$): 3213, 3161 (N—H), 1653, 1613 (C=O), 1382 (COO$^-$), 1260 (CH$_3$), 1031 (C—O—C), 420 (Pt-N). $^1$HNMR (D$_2$O, δ/ppm): 0.60 (d, 4H, 2-CH2), 0.75 (d, 4H, CH2) 1.75 (s, 4H, H-2 & H-3), 2.02 (s, 2H, H-5 & H-6), 2.38 (m, 2H, 2—CH), 4.04 (s, 2H, H-1 & H-4).

EXAMPLE 8

Synthesis of Compound Having Structure II, (—A—A—=—NH$_2$—CH$_2$—CH$_2$—NH$_2$—) . . . (7)

K$_2$PtCl$_4$ (0.5487 g, 1.322 mmol) was dissolved in water (10 ml) and NH$_2$CH$_2$CH$_2$NH$_2$ (en) (0.0793 g, 1.332 mmol, dissolved in 1 ml water) was added and stirred at RT for 6–8 hr. The mixture was then kept at 0° C. overnight, filtered, and the yellow ppt was washed with water, ethanol and ether before being air-dried. Yield produced was 0.388 g, 90%.

AgNO$_3$ (0.3634 g, 2.137 mmol) and Pt(en)Cl$_2$ (0.3484 g, 1.069 mmol), and water (10 ml) were added together and mixture stirred in the dark for 18 hr, after which the solution was filtered. Ligand B (0.1796 g, 1.069 mmol) and NaOH (0.086 g, 2.137 mmol) were added to the filtrate and mixture stirred at RT for 16 hr. Water was removed in vacuo and the grey solid was washed with water (5 ml), ethanol and ether. Final yield of product was 0.23 g (50%)

IR (KBr, cm$^{-1}$): 3281, 3207, 3131 (N—H), 1628, 1604 (C=O), 1381 (COO$^-$), 1258, 1170, 1055, 934 (C—O—C), 410 (Pt-N). $^1$H NMR (D$_2$O, δ/ppm): 1.75 (q, 4H, H-2 & H-3), 2.54 (d, 4H, H-7 & H-8), 3.55 (s, 2H, H-5 & H-6), 4.56 (d, 2H, H-1 & H-4). $^{13}$C NMR (D$_2$O, δ/ppm): 30.32 (C-2 & C-3), 51.06 (C-7 & C-7') 59.41 (C-5 & C-6), 81.64 (C-1 & C-4).

EXAMPLE 9

Synthesis of Compound Having Structure II, (—A—A—=—NH$_2$—CH$_2$—CH$_2$—CH$_2$—NH$_2$—) . . . (8)

K$_2$PtCl$_4$ (0.4744 g, 1.143 mmol) was dissolved in water (10 ml) and NH$_2$CH$_2$CH$_2$CH$_2$NH$_2$ (pn) (0.0846 g, 1.143 mmol, dissolved in 1 ml water) was added and stirred at RT for 6–8 hr. The mixture was then kept at 0° C. overnight, filtered, and the yellow ppt was washed with water, ethanol and ether before being air-dried. Yield produced was 0.31 g, 80%.

AgNO$_3$ (0.2404 g, 1.414 mmol) and Pt(pn)Cl$_2$ (0.2404 g, 0.707 mmol), and water (10 ml) were added together and mixture stirred in the dark for 18 hr, after which the solution was filtered. Ligand B (0.1188 g, 0.707 mmol) and NaOH (0.0566 g, 1.414 mmol) were added to the filtrate and mixture stirred at RT for 16 hr. Water was removed in vacuo and the grey solid was washed with water (5 ml), ethanol and ether. Final yield of product was 0.22 g (65%).

IR (KBr, cm$^{-1}$): 3175, 3090 (N—H), 1662, 1633 (C=O), 1388 (COO$^-$), 1265, 1203, 939, 415 (Pt-N). $^1$H NMR (D$_2$O, δ/ppm): 1.18 (t, 2H, H-8), 1.72 (s, 4H, H-2 & H-3), 2.04 (s, 2H, H-5 & H-6), 2.68 (m, 4H, H-7 & H-9), 3.47 (s, 2H, H-1 & H-4).

EXAMPLE 10

Synthesis of Compound Having Structure II, (—A—A—=trans-diaminocyclohexyl, DACH) . . . (9)

K$_2$PtCl$_4$ (1 g, 2.410 mmol) was dissolved in water (10 ml), and trans-diamine cyclohexane (DACH) (0.2747 g, 2.410 mmol, dissolved in 1 ml of H$_2$O) was added dropwise; a yellow ppt was subsequently formed. The mixture was stirred at RT for 6~8 h, then filtered, washed with water (5 ml). ethanol (5 ml) and diethyl ether (5 ml), before being air dried.

AgNO$_3$ (0.3579 g, 2.1053 mmol) and Pt(DACH)Cl$_2$ (0.4 g, 1.0526 mmol) were placed into a reaction flask with water (20 ml) and stirred in the dark for 18 h. The mixture was then filtered and solid AgCl removed. Ligand B (0.1768 g, 1.0526 mmol) and NaOH (0.0842 g, 1.1053 mmol) was added into the filtrate containing Pt(DACH)(NO$_3$)$_2$ and the mixture was allowed to stir at RT for 16 h. A grey solid was formed and water was removed in vacuo. The solid was washed with ice water (5 ml), ethanol (5 ml) and diethyl ether (5 ml) before air drying. Yield obtained was 0.22g (42%).

IR (KBr, cm$^{-1}$): 3195, 3150 (N—H), 1642, 1608 (C=O), 1396 (COO$^-$), 1267, 1214, 1066, 940 (C—C—C). $^1$H NMR (D$_2$O, δ/ppm): 1.17 (m, 2H, H-2'a & H-3'a), 1.31 (d, 2H, H-1'a & H-4'a), 1.59 (d, 2H, H-2'b & H-3'b), 1.74 (d, 2H, H-2 & H-3), 2.05 (d, 2H, H-1'b & H-4'b), 2.37 (d, 2H, H-5'& H-6'), 3.99 (q, 2H, H-6 & H-6), 4.86 (s, 2H, H-1 & H-4). $^{13}$C NMR (D$_2$O, δ/ppm): 26.61 (C-2' & C-3'), 30.15 (C-2 & C-3), 34.40 (C-1' & C-4'), 59.31 (C-5 & C-6), 65.09, 65.57 (C-5' & C-6'), 81.42 (C-1 & C-4), 183.77 (C=O).

EXAMPLE 11

Synthesis of Compound Having Structure II, (—A—A—=—(C$_2$H$_4$—OH)NH—CH$_2$—CH$_2$—NH (C$_2$H$_4$OH) . . . (10)

K$_2$PtCl$_4$ (0.5214 g, 1.26 mmol) was dissolved in water (5 ml), and N, N'-bis(2-hydroxyethyl)ethylenediamine) (enOH) (0.1310 g, 1.26 mmol) added. The mixture was stirred at RT for 6~8 h, then filtered, washed with water (5 ml). ethanol (5 ml) and diethyl ether (5 ml), before being air dried, yield: 0.3963 g, 85%.

AgNO$_3$ (0.3437 g, 2.02 mmol) and Pt(enOH)Cl$_2$ (0.3740 g, 1.01 mmol) were placed into a reaction flask with water (5 ml) and stirred in the dark for 18 h. The mixture was then filtered and solid AgCl removed. Ligand B (0.1700 g, 1.01 mmol) and NaOH (0.0808 g, 2.024 mmol) was added into the filtrate and the mixture was allowed to stir at RT for 6 h. A grey solid was formed and water was removed in vacuo. The solid was washed with ice water (5 ml), ethanol (5 ml) and diethyl ether (5 ml) before drying in a dessicator with P$_2$O$_5$. Yield obtained was 0.38 g (40%).

IR (KBr, cm$^{-1}$): 3573, 3304 (O—H, 3213, 3157 (N—H), 1627, 1368 (COO$^-$), 1259, 1214, 1064, 1038, 936 (C—O—C).

EXAMPLE 12

Physicochemical Properties of the Newly Synthesized Complexes

The purity of the synthesized new complexes were analysed by HPLC and MS. Table 1 shows the HPLC conditions and the % purity. Table 2 shows the physicochemcial properties.

TABLE 1

HPLC Conditions and % Purity of Complexes

| Example | Mobile phase Water: CH$_3$OH | Flow rate ml/min | Retention time t$_R$/min | % Purity |
|---|---|---|---|---|
| 2 | water | 1 | 6.07 | 100 |
| 3 | 1:1 | 1 | 5.46 | 97 |
| 4 | 1:1 | 1 | 5.86 | 100 |
| 5 | 9:1 | 1 | 8.88 | 95 |
| 6 | 9:1 | 1 | 8.79 | 100 |
| 7 | 1:1 | 1 | 4.53 | 98 |
| 8 | 9:1 | 1 | 8.84 | 98 |
| 9 | 8:1 | 1 | 7.48 | 98 |
| 10 | 1:1 | 1 | 5.60 | 96 |
| 11 | 8:1 | 1 | 4.87 | 100 |

TABLE 2

Physicochemical Properties of the Novel Complexes

| | | | Elemental Analysis | | | | | | FAB-MS | |
|---|---|---|---|---|---|---|---|---|---|---|
| | Yield | Sol. (aq) | C | | H | | N | | (m/z) | |
| Cpd | % | mg/ml | exp. | calc. | exp. | calc. | exp. | calc. | theory | expt. |
| 2 | 58 | 186 | 23.45 | 23.25 | 3.48 | 3.41 | 6.75 | 6.27 | — | — |
| 3 | 40 | 89 | 26.26 | 27.21 | 4.00 | 4.11 | 6.11 | 6.34 | 442.355 | 442.093 |
| 4 | 45 | 11.2 | 29.26 | 30.71 | 4.98 | 4.72 | 5.74 | 5.97 | 470.409 | 470.124 |
| 5 | 45 | 5.1 | 33.55 | 33.80 | 5.23 | 5.27 | 5.72 | 5.63 | — | — |
| 6 | 39 | 5.1 | 32.88 | 33.80 | 5.15 | 5.27 | 5.65 | 5.63 | 498.374 | 498.156 |
| 7 | 35 | 2.2 | 33.37 | 34.08 | 4.56 | 4.49 | 5.54 | 5.67 | 494.125 | 494.126 |
| 8 | 50 | 11.3 | 26.04 | 27.34 | 3.90 | 3.67 | 6.01 | 6.37 | 440.078 | 440.078 |
| 9 | 65 | 1.4 | 29.23 | 29.14 | 4.01 | 4.00 | 6.12 | 6.18 | — | — |
| 10 | 41 | 2.6 | 32.09 | 34.08 | 4.39 | 4.49 | 5.50 | 5.67 | — | — |
| 11 | 40 | 4.1 | 29.03 | 31.88 | 4.74 | 4.59 | 4.83 | 5.31 | 528.130 | 528.130 |

EXAMPLE 13

Antitumor Activity of Example 2, a Representative Complex

The antitumor activity of these novel drugs, represented by Example 2, towards human leukaemia cell lines J$_{6-2}$ and K$_{562}$, and lymphocyte and leukaemia cell line R$_{aji}$ is described. Antitumor cells were grown in complete medium at 37° C. in an atmosphere of 5% CO$_2$ and 100% humidity. Trypsinized cells were adjusted to a concentration of 1–4× 10$^5$ cells/ml and 0.1 ml of the cell suspension was added to a 96-well microculture plate and incubated under standard conditions. Drug (a series of log dilutions) and complete medium (control), 0.1 ml, were added to the wells. Each drug concentration consisted of six replicates while the number of control cultures equaled 12 times the number of tested drug. The cultures were incubated for an additional 48 hours. The MTT (tetrazolium, 10 µl, 0.05 mg) assay was used to determine the growth-inhibitory effects of the drug. The amount of reduced MTT was determined by spectrophotometric means (Bio-RAD Model 3550). The concentration of drug resulting in 50% growth inhibition (IC$_{50}$) was determined. Calculation:

$$\% \text{ inhibition} = \frac{\text{control cells OD} - \text{test cells OD}}{\text{control cells OD}} \times 100\%$$

The results are as shown in Table 3. The results show this complex has high activity towards inhibition of the three cancer cell lines.

TABLE 3

| | In vitro % inhibition activity of Example 2 (MTT assay) | | |
|---|---|---|---|
| | Dose | | |
| Cell | 100 (μl/ml) | 10 (μl/ml) | 1 (μl/ml) |
| $K_{562}$ | >75% | >75% | 25–50% |
| $R_{aji}$ | >75% | >75% | <25% |
| $J_{6-2}$ | >75% | >75% | 50–75% |

EXAMPLE 14

Toxicity Testing

The toxicity tests used ICR mice (30–40 g), each group containing 12–13 mice. Example 2 was used as a representative complex, and cisplatin and carboplatin were used as controls. The test and control compounds were dissolved in 0.9% NaCl to an appropriate concentration. For each compound, 6–8 doses were tested and the injection volume varied between 2–2.5 ml. animals were observed for 6 days. The results are as shown in Table 4.

TABLE 4

| | Comparison of Solubility and $LD_{50}$ between Cisplatin, Carboplatin and Example 2 | | |
|---|---|---|---|
| | Cisplatin | Carboplatin | Example 2 |
| Solubility | 1–3 mg/ml | 10 mg/ml | 5.0 mg/ml |
| $LD_{50}$ | 12 mg/kg | 190 mg/kg | 240 mg/kg |

From Table 4, the Invention, represented by Example 2, showed better aqueous solubility than cisplatin and significantly lower toxicity than cisplatin and carboplatin. Therefore, this compound, Example 2, has potential to be a new type of platinum antitumor drug.

Second Series of Experiments

Ligand B (demethyl cantharidin)

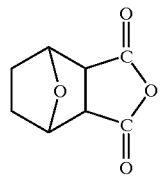

Ligand B (demethyl cantharidin)

-continued

Cantharidin

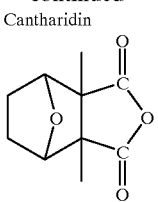

Cantharidin

STRUCTURES OF CARBOPLATIN AND CISPLATIN

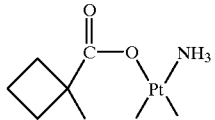

Carboplatin

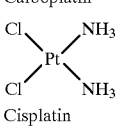

Cisplatin

Ligand B is a synthethic derivative of cantharidin, which is extracted from *Epicanta gorhami* Mars or Mylabris. There are two types of Mylabris commonly used in traditional Chinese medicine (TCM); *Mylabris phalerata* Pall and *M. cichorii* L. As a TCM, cantharidin is mainly used for ailments of the liver, lung, intestinal and digestive tracts. However, cantharidin has severe side-effects such as nausea, vomiting and diarrhoea. Other side effects may include high heart rate and numbness of fingers and face.

The reasons for selecting demethyl cantharidin as a ligand for the synthesis of a novel series of platinum complex as potential third generation antitumor agents are as follows:

i) It is structurally similar to cantharidin, therefore should present similar structure-activity relationship (SAR). The novel platinum complex may be specifically active towards liver cancers and leukaemia.

ii) It may have lower toxicity than cantharidin.

iii) The overall structure of Compound A (Structure I, R=H) structurally resembles that of carboplatin, an established second generation platinum antitumor drug.

EXPERIMENTAL

PREPARATION OF LIGANDS

Ligand A
7-oxabicyclo[2, 2, 1]-2-heptene-5, 6-dicarboxylic acid anhydride

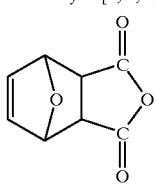

Furan (5.4 ml, 0.073 mol) and maleic anhydride (6 g, 0.061 mol) were placed into a dry beaker with THF (8 ml) and contents stirred at room temperature for 60 minutes.

Solvent was removed in vacuo, and the crude material recrystallized from ethyl acetate. White crystals of compound A were obtained (9.1 g, 88% yield).

Melting point: 123.5~124.5° C. $^1$H NMR (CDCl$_3$), δ/ppm: 6.58 (t, 2H, H-2 & H-3) 5.46 (t, 2H, H-1 & H-4) 3.17 (s, 2H, H-5 & H-6)

The compound was characterized spectroscopically by mass analysis.

ii. Ligand B
7-oxabicyclo[2, 2, 1]-heptane-5, 6-dicarboxylic acid anhydride

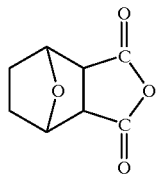

Cpd A (2 g, 0.012 mol) was dissolved in ethyl acetate (30 ml) and Pd-C catalyst (5% Pd, 0.2 g) was added. The reaction mixture was stirred, refluxed and hydrogen gas bubbled into the reaction flask at atmospheric pressure for 6 hours. Solvent was removed in vacuo and a white solid was obtained. Compound B was recrystallized from ethanol (1.7 g, 85%).

Melting point: 115.9~116.1° C. $^1$H NMR (CDCl$_3$), δ/ppm: 5.04 (m, 2H, H-1 & H-4); 3.18 (s, 2H, H-5 & H-6); 1.89 (m, 2H, H-2 & H-3); 1.65 (m, 2H, H-2' & H-3')

The compound was characterized spectroscopically by mass analysis.

SYNTHESIS OF NOVEL PLATINUM COMPLEXES

1. Synthesis of Compound A (Structure I, R=H)

For 1 g of starting material, synthesis was as follows:

i). H$_2$PtCl$_6$. 4.5H$_2$O (1 g, 1.93 mmol) was dissolved in water (15 ml), heated to 60° C., and a solution of N$_2$H$_4$. 2HCl (0.1 g in 5 ml water, 0.95 mmol) was added dropwise. Ten minutes later, KCl (0.32 g, 4.1 mmol) was added and reaction mixture stirred for 30 minutes. KI (1.92 g, 11.6 mmol) was added into the solution and mixture was allowed to react in the dark for 15 minutes at 80° C. The reaction system was cooled to 40° C. and NH$_3$ (aq, 30%) was added dropwise, keeping the pH <7. A dark yellow precipitate was formed and NH$_3$ (aq, 30%) was continuously added until pH remained at 8. The reaction mixture was stirred at 40° C. for 2 hrs, then filtered and precipitate washed with water (5 ml), ethanol (5 ml) and diethyl ether (5 ml). (NH$_3$)$_2$PtI$_2$ was recrystallized from DMF (0.37 g, 45%).

ii). (NH$_3$)$_2$PtI$_2$ (0.483 g, 1 mmol) and AgNO$_3$ (0.34 g, 2 mmol) were placed into a beaker with water (25 ml). The reaction mixture was stirred in the dark at RT for 16 hrs, filtered and solid AgI removed. (NH$_3$)$_2$Pt(NO$_3$)$_2$ remains in solution.

Analytical HPLC (column: SODS, 4.6 mm×25 cm; MP: water; flow rate: 1 ml/min)

$t_R$ (min): 2.585 (single peak)

iii). Ligand B (0.168 g, 1 mmol) and NaOH (0.08 g, 2 mmol) was added into the filtrate containing (NH$_3$)$_2$Pt(NO$_3$)$_2$ and mixture was allowed to stir at RT for 8 hrs. A white solid precipitate was formed, filtered and washed with ice water (5 ml), ethanol (5 ml) and diethyl ether (5 ml) to give Compound A (0.28 g, 58%).

Decomposition point: 248.0~249.0° C.

Solubility in water: 4.553.0 mg/ml at RT, pH~6

Analytical HPLC (column: 5 ODS, 4.6 mm×25 cm; MP: water; flow rate: 1 ml/min)

$t_R$ (min): 6.07 (single peak)

$^1$H NMR (D$_2$O), δ/ppm: 1.72 (s, 2H, H-2 & H-3) 4.02 (s, 2H, H-5 & H-6) 4.92 (s, 2H, H-1 & H-4)

The compound was characterized spectroscopically by mass analysis.

2. Synthesis of Compound B (Structure I, R=(CH(CH$_3$)$_2$)

For 1 g of starting material, synthesis was as follows:

i) H$_2$PtCl$_6$.5H$_2$O (1 g, 2 mmol) was dissolved in water (10 ml), heated to 60° C. and a solution of N$_2$H$_4$. 2HCl (0.107 g in 5 ml water, 1 mmol) was added dropwise. Fifteen minutes later, KCl (0.328 g, 4.4 mmol) was added and the reaction mixture was stirred for 30 minutes. KI (1.59 g, 9.6 mmol) was added into the solution, heated to 80° C. The mixture was allowed to react in the dark for 15 minutes, followed by cooling to 50° C., and i-PrNH$_2$ (0.826 g in 5 ml water, 14 mmol) was added dropwise. A dark yellow precipitate was formed and the mixture was stirred at 60° C. for 4 h, then kept at 0° C. for 4 h. The mixture was filtered and the ppt washed with water (10 ml), ethanol (10 ml) and diethyl ether (10 ml), then air-dried.

ii) Pt (i-PrNH$_2$).2,2 (0.5616 g, 0.99 mmol) and AgNO$_3$ (0.3368 g, 0.198 mmol) were placed in a beaker with 20 ml water. The mixture was stirred in the dark for 16 h, filtered and the solid removed.

iii) Ligand B (0.1663 g, 0.99 mmol) and NaOH (0.198 mmol) were added into the solution and stirred at RT for 9 h. The mixture was distilled in vacuo and a white solid was obtained, which was washed with ice-water (10 ml), ethanol (10 ml) and diethyl ether (10 ml). The yield of product Compound B was 0.19 g, 39%.

Solubility in water: 5.1 mg/ml, pH~6 Analytical HPLC: Column (50DS, 4.6 mm×25 cm); MP (H$_2$O), flow rate (1 ml/min).

$t_R$: 8.79 min (single peak, 98%)

| $^1$H NMR (D$_2$O), | δ$_H$/ppm: 1.34(d, 6H, 2CH$_3$) | δ$_C$/ppm: 24.95(CH$_3$) |
|---|---|---|
| | 1.35(d, 6H, 2CH$_3$) | 25.17(CH$_3$) |
| | 1.75(m, 4H, H-2, H-3) | 30.13 (C-2, C-3) |
| | 2.90(sept, 2H, C<u>H</u>, iPr) | 51.11(<u>C</u>H, iPr) |
| | 3.91(s, 2H, H-5, H-6) | 59.06(C-5, C-6) |
| | 4.95(d, 2H, H-1, H-4) | 81.48(C-1, C-4) |
| | | 183.63(C=O) |

The compound was characterized spectroscopically by mass analysis.

3. Synthesis of Compound C (Structure I, R=CH$_3$)

i) K$_2$PtCl$_4$ (0.9959 g, 2.40 mmol) was dissolved in water (10 ml). The solution was heated to 80° C., then KI (1.9104 g, 0.0115 mol) was added and mixture allowed to react for 15 mins. The dark mixture was cooled to 50° C. and 35% CH$_3$NH$_2$ (0.4251 g, 4.8 mmol) was added dropwise and a yellow ppt was formed immediately. The reaction mixture was kept at 60° C. for 3–4 hr, cooled to RT, filtered and ppt washed with water (5 ml) and ethanol (5 ml) before being air dried. Yield: 1.13 g (92%).

Pt(CH$_3$NH$_2$)$_2$I$_2$ (1.1073 g, 1.99 mmol) and AgNO$_3$ (0.6769 g, 3.98 mmol) were placed into the reaction flask with water (10 ml). The mixture was stirred in the dark for 24 hr, filtered and solid AgI removed.

iii) Ligand B (0.3343 g, 1.99 mmol) and NaOH (0.1592 g, 3.98 mmol) were added into the solution of Pt (MeNH$_2$)$_2$(NO$_3$)$_2$ and mixture was allowed to stir at RT for 2 days. Water was removed in vacuo and the resultant grey solid washed with ice water (5 ml). Yield of product at this stage was 0.17 g (19%).

The water wash layer was collected and a small amount of methanol added which resulted in the appearance of a white ppt. NMR analysis revealed this ppt to be unreacted Ligand B. The volume of the remaining filtrate was reduced down to 1 ml and the contents kept in the dessicator with a beaker of P$_2$O$_5$. Two days later, a light yellow crystalline product was formed and washed with a small amount of ice water. The yield of product Compound C was 0.18 g (21%).

Total yield of product was 0.35 g (40%). Solubility in water: 186.00 mg/ml, RT, pH~6 Analytical HPLC (column: 5 ODS, 4.6 mm×25 cm; MP: water:methanol, 1:1; flow rate: 1 ml/min t$_R$ (min): 5.46 (97%)

The compound was characterized spectroscopically by mass analysis.

$^1$H NMR (D2O), δ/ppm 1.65 (s, 4H, H-2 & H-3) 2.21 (s, 6H, 2-CH$_3$) 3.86 (s, 2H, H-5 & H-6) 4.85 (s, 2H, H-1 & H-4) 13C NMR (D$_2$O), δ/ppm: 31.05 (C-2 & C-3) 35.57 (CH$_3$) 59.36 (C-5 & C-6) 81.74 (C-1 & C-4) 184.04 (C=O)

4. Synthesis of Compound D (Structure I, R=C$_2$H$_5$)

i) K$_2$PtCl$_4$ (1.1025 g, 2.66 mmol) was dissolved in water (10 ml). KI (2.2961 g, 13.8 mmol) was added to the solution. The mixture was stirred at 80° C. for 15 mins, followed by cooling to 50° C., before 70% C$_2$H$_5$NH$_2$ (0.342 g, 5.32 mmol) was added, pH~8. The reaction mixture was stirred at 60° C. for 4 hr, then filtered and ppt washed with water (5 ml) and ethanol (5 ml). Yield obtained was 1.3 g (93%).

ii) Pt(EtNH$_2$)$_2$I$_2$ (1.2118 g, 2.25 mmol) and AgNO$_3$ (0.7644 g, 4.5 mmol) were placed in the reaction flask with water (10 ml). The mixture was stirred in the dark at RT for 24 hr, filtered and AgI removed.

iii) Ligand B (0.360 g, 2.25 mmol) and NaOH (0.180 g, 4.5 mmol) was added to the filtrate and the mixture allowed to stir at RT for 2 days. Water was removed in vacuo and the solid was washed with ice water (5 ml). Product yield was 0.4 g.

The water wash layer was collected and the volume reduced to 1 ml. This sample was then kept in the dessicator with a beaker of P$_2$O$_5$. A light yellow crystalline product was formed which was filtered and washed with water (5 ml). Product Compound D was 0.06 g.

Total product yield was 0.46 g (45%) Solubility in water: 98.00 mg/ml, RT, pH~6 Analytical HPLC (column: 5 ODS, 4.6 mm×25 cm; MP: water:methanol, 1:1; flow rate: 1 ml/min) t$_R$ (min): 5.862 (99%) The compound was characterized spectroscopically by mass analysis.

$^1$H NMR (D$_2$O), δ/ppm: 1.13 (t, 6H, H-8 & H-10) 1.62 (s, 4H, H-2 & H-3); 2.50 (q, 4H, H-7 & H-9); 3.82 (s, 2H, H-5 & H-6); 4.82 (s, 2H, H-1 & H-4); $^{13}$C NMR (D$_2$O), δ/ppm 17.86 (C-8 & C-10); 30.31 (C-2 & C-3); 44.40 (C-7 & C-9); 59.35 (C-5 & C-6); 81.71 (C-1 & C-4); 183.93 (C=O);

5. Synthesis of Compound Having Structure I, R=C$_3$H$_7$ i) K$_2$PtCl$_4$ (0.8458 g, 2.038 mmol) was dissolved in water (8 ml) and heated to between 70–80° C. KI (2.0298 g, 12.228 mmol) was added and mixture stirred for 15 mins. The resultant black solution was cooled to 50° C. and n-propylamine (0.2405 g, 4.076 mmol dissolved in 1 ml H$_2$O) was added to give a yellow ppt. The reaction was allowed to stir at 60° C. for a further 3–4 hr before being cooled and kept at 0° C. overnight. The mixture was then filtered, washed with water (5 ml) and air dried. Yield of product was 80%.

ii) Pt(nPrNH$_2$)$_2$I$_2$ (0.532 g, 0.938 mmol), AgNO$_3$ (0.319 g, 1.877 mmol) and water (8 ml) were added together and mixture stirred in the dark for 18 hr. The mixture was filtered and a filtrate containing Pt(nPrNH$_2$)$_2$(NO$_3$)$_2$ was obtained.

iii) Ligand B (0.1576 g, 0.938 mmol) and NaOH (0.075 g, 1.877 mmol) were added to the filtrate and the reaction mixture stirred at RT for 18 hr whereby a white ppt was formed. The water was removed in vacuo and the solid washed with ice water (5 ml), ethanol (5 ml) and diethyl ether (5 ml). Yield of the final product was 0.209 g (45%).

Solubility: 11.2 mg/ml , 37° C., pH~6 Analytical HPLC (column: 5 ODS, 4.6 mm×25 cm; MP: water:methanol, 9:1; flow rate: 1 ml/min) t$_R$: 8.883 min (95%)

The compound was characterized spectroscopically by mass analysis.

$^1$H NMR (D$_2$O), δ/ppm: 0.94 (t, 6H, H-9 & H-9') 1.70 (hextet, 4H, H-8 & H-8'); 1.75 (q, 4H, H-2 & H-3); 2.54 (t, 4H, H-7 & H-7'); 3.92 (s, 2H, H-5 & H-6); 4.94 (d, 2H, H-1 & H-4); $_{13}$C NMR (D$_2$O), δ/ppm: 13.18 (C-9 & C-9'); 26.26 (C-8 & C-8'); 30.34 (C-2 & C-3); 51.36 (C-7 & C-7'); 59.36 (C-5 & C-6); 81.69 (C-1 & C-4); 183.92 (C=O)

6. Synthesis of Compound Having Structure II, —A—A—=—NH$_2$—CH$_2$CH$_2$—NH$_2$— i) K$_2$PtCl$_4$ (0.5487 g, 1.322 mmol) was dissolved in water (5 ml) and NH$_2$CH$_2$CH$_2$NH$_2$ (en)(0.0793 g, 1.332 mmol, dissolved in 1 ml water) was added and stirred at RT for 6–8 hr. The mixture was then kept at 0° C. overnight, filtered, and the yellow ppt was washed with water, ethanol and ether before being air-dried. Yield produced was 90%.

ii) Pt(en)Cl$_2$ (0.3484 g, 1.069 mmol), AgNO$_3$ (0.3634 g, 2.137 mmol) and water (8 ml) were added together and mixture stirred in the dark for 18 hr, after which the solution was filtered. Pt(en)(NO$_3$)$_2$ was obtained in solution.

iii) Ligand B (0.1796 g, 1.069 mmol) and NaOH (0.086 g, 2.137 mmol) were added to the filtrate from (ii) and mixture stirred at RT for 10 hr. Water was removed in vacuo and the grey solid was washed with water, ethanol and ether.

Final yield of product was 0.23 g (50%) Solubility in water: 11.3 mg/ml, 37° C., pH~6 Analytical HPLC (column: 5 ODS, 4.6 mm×25 mm; MP: water:methanol, 9:1; flow rate: 1 ml/min) t$_R$ (min): 8.838 min (98%)

The compound was characterized spectroscopically by mass analysis.

$^1$H NMR (D$_2$O), δ/ppm: 1.75 (q, 4H, H-2 & H-3) 2.54 (d, 4H, H-7 & H-8); 3.99 (s, 2H, H-5 & H-6); 4.93 (d, 2H, H-1 & H-4); $^{13}$C NMR (D$_2$O), δ/ppm: 30.32 (C-2 & C-3); 51.06 (C-7 & C-8); 59.41 (C-5 & C-6); 81.64 (C-1 & C-4)

7. Synthesis of Compound Having Structure II, (—A—A—=trans-diaminocyclohexyl, DACH)

For 1 g of starting material, synthesis was as follows:

i) K$_2$PtCl$_4$ (1 g, 2.410 mmol) was dissolved in water (15 ml), and trans-diamine cyclohexane (DACH) (0.2747 g, 2.410 mmol) was added dropwise; a yellow ppt was subsequently formed. The mixture was stirred at RT for 8 h and kept at 0° C. for a further 24 h. The mixture was then filtered, washed with water (5 ml). ethanol (5 ml) and diethyl ether (5 ml), before being air dried.

ii) Pt(DACH)Cl$_2$ (0.4 g, 1.0526 mmol) and AgNO$_3$ (0.3579 g, 2.1053 mmol) were placed into a reaction flask with water (20 ml) and stirred in the dark for 16 h. The mixture was then filtered and solid AgCl removed; Pt (DACH)(NO$_3$)$_2$ remained in the solution.

iii) Ligand B (0.1768 g, 1.0526 mmol) and NaOH (0.0842 g, 2.1053 mmol) was added into the filtrate containing Pt(DACH)(NO$_3$)$_2$ and the mixture was allowed to stir at RT for 8 h. A grey solid was formed and water was removed in vacuo. The solid was washed with ice water (5 ml), ethanol (5 ml) and diethyl ether (5 ml) before air drying. Yield obtained was 0.2137 g (41%). Solubility in water: 2.6 mg/ml

TABLE 1

Summary of solubility data: Table 1

| Compound | Solubility in water (mg/ml) |
|---|---|
| Cisplatin | 2.00 |
| Carboplatin | 10.00 |
| A | 4.55 |
| B | 5.10 |
| C | 186.00 |
| D | 98.00 |

In Vitro Antitumor-drug Screening

Test compounds A–D, together with controls cisplatin and carboplatin, were screened for in vitro antitumor activity against a series of human cancer cell lines and mouse leukaemia L1210, using a tetrazolium microculture assay.

Drugs: Drugs to be tested were dissolved in complete medium at twice the highest concentration to be used, followed by filter (0.22 μm) sterilization. A series of log dilutions were made of each drug solution using complete medium and stored at r.t. until use.

Cells: L1210, H-522 (human lung), HT-29 (human colon), Hela, CC3 (human cervix) were obtained from the American Type Culture Collection (ATCC). CNE-1 and CNE-2 (human nasopharyngeal) were obtained from The Hong Kong Cancer Institute, The Chinese University of Hong Kong.

In vitro drug exposure: Trypsinised cells were adjusted to a concentration of 3×10$^4$ cells/ml in complete medium and for each drug to be tested, 0.1 ml of the cell suspension was added to each of 48 wells of a 96-well microculture plate. The plate was then incubated at standard conditions for 24 hours in order to allow the cells to attach to the bottom of the well. To each well of the control cultures, 0.1 ml of complete medium was added. Each drug/concentration combination consisted of six replicates while the number of control cultures equaled 12 times the number of tested drugs. The cultures were incubated for an additional 48 hours.

MTT assay: The MTT (tetrazolium) assay was used to determine the growth-inhibitory effects of different drugs. A 5 mg/ml solution of MTT (3-(4,5-dimethylthiazol-2-yl)-2,5-diphenyltetrazolium bromide) was prepared in complete medium, filter (0.22 μm) sterilized and stored at 4° C. To each well, 0.02 ml of the MTT solution was added and the plates were then incubated at standard conditions for 4 hours at which time the media from each well was removed and 0.1 ml of acetic acid in SDS was added to each well to solubilize the colored dye produced from the metabolic reduction of MTT. The amount of reduced MTT was determined by spectrophotometric means (540 nm).

Data analysis: The mean OD for all 48 control wells was determined. For each concentration of each drug, the mean OD of the 6 wells was determined and the "Percent of Control" values were determined and plotted. The concentration of drug resulting in 50% growth inhibition (IC$_{50}$) was determined by visual inspection of the resulting graphs.

Results are as shown in Table 2.

TABLE 2

In vitro antitumor activity IC50 (μM)

| | | IC50 (μM) | | | | |
|---|---|---|---|---|---|---|
| Cell | Cpd:Cisplatin | Carbo | A | B | C | D |
| CC3 | 6.253 | 205.000 | 19.600 | 47.767 | 33.200 | 49.600 |
| CNE-1 | 6.363 | 173.875 | 28.425 | 45.850 | 44.375 | 36.575 |
| CNE-2 | 6.045 | 126.500 | 20.825 | 29.765 | 24.925 | 29.275 |
| H522 | 12.083 | 287.000 | 29.823 | 121.300 | 105.667 | 72.800 |
| Hela | 8.560 | 244.500 | 27.775 | 99.225 | 66.725 | 36.575 |
| HT29 | 38.267 | 733.500 | 59.133 | 69.467 | 40.200 | 58.600 |
| L1210 | 1.634 | 48.827 | 11.373 | 21.835 | 16.825 | 23.425 |

In Vivo Toxicity Studies

Toxicological studies in animals is one of the most important experiments required for the development of novel drugs intended for clinical use. The results generated from these studies will advance the knowledge on the suitability of these novel drugs for use in human patients.

1. LD$_{50}$:

Drugs:

| Tests | Controls |
|---|---|
| A, B, C, D | cisplatin, carboplatin |

Animals: ICR mice, male, 30 g, 10 animals per test/control group.

Dose: Test/control drug were dissolved in normal saline. Four doses, each increasing by 10–20% were injected intraperitoneally into mice. 10 mice were used for each dose point.

Results: A 4-point curve was created for each drug and the LD$_{50}$ (dose of drug which caused death to 50% of test animals) estimated. The results are as shown in Table 3.

TABLE 3

| Compound | LD$_{50}$ (mg/kg) |
|---|---|
| Cisplatin | 12.76 |
| Carboplatin | 203.20 |
| A | 238.30 |
| B | 117.80 |
| C | 450.80 |
| D | 307.10 |

2. 5-Day Parenteral Acute Toxicity Trial:

Drugs:

| Tests | Controls |
|---|---|
| A, B | cisplatin, carboplatin |

Animals: ICR mice, 4 to 6 weeks old, 6 male and 6 female for test drugs; 8 male and 8 female for controls.

Conditions: Temperature: 22° C.±3° C.; Relative humidity: 30–70 T; Light: 12:12. Animals were housed in twos or threes depending on group numbers.

Dose: 1/12 $LD_{10}$ (anticipated maximum tolerated dose, MTD for humans), in large volume (0.5–1.0 ml of saline) administered i.p. every 24 hours for 5 days.

Results: Animals were sacrificed on the 6th day and tissue slices were obtained of the various internal organs, in particular liver and kidney. Histopathology of liver and kidney were examined for each animal. Table 4 shows a summary of the observations.

TABLE 4 (A)

HISTOPATHOLOGY STUDIES OF VARIOUS COMPOUNDS WITH DOSE OF $1/_{12}LD_{10}$

| KIDNEY Drug | No. | Sex | Normal | Protein casts | Nephrosis |
|---|---|---|---|---|---|
| Saline | 1 | M | √ | | |
| | 2 | M | √ | | |
| | 3 | M | √ | | |
| | 4 | M | √ | | |
| | 5 | F | √ | | |
| | 6 | F | √ | | |
| | 7 | F | | + | |
| | 8 | F | | + | |
| Cisplatin | 1 | M | √ | | |
| | 2 | M | √ | | |
| | 3 | M | √ | | |
| | 4 | M | √ | | |
| | 5 | F | √ | | |
| | 6 | F | √ | | |
| | 7 | F | √ | | |
| | 8 | F | √ | | |
| Carboplatin | 1 | M | √ | | |
| | 2 | M | √ | | |
| | 3 | M | √ | | |
| | 4 | M | √ | | |
| | 5 | M | √ | | |
| | 6 | F | √ | | |
| | 7 | F | √ | | |
| | 8 | F | √ | | |
| | 9 | F | | + | |
| TCM | 1 | M | √ | | |
| | 2 | M | √ | | |
| | 3 | M | √ | | |
| | 4 | M | √ | | |
| | 5 | M | √ | | |
| | 6 | F | √ | | |
| | 7 | F | √ | | |
| | 8 | F | | + | |
| | 9 | F | | + | |
| Compound A | 1 | M | √ | | |
| | 2 | M | √ | | |
| | 3 | M | √ | | |
| | 4 | M | √ | | |
| | 5 | M | √ | | |
| | 6 | M | √ | | |
| | 7 | F | √ | | |
| | 8 | F | √ | | |
| | 9 | F | | + | |
| | 10 | F | | + | |
| | 11 | F | | + | |
| | 12 | F | √ | | |
| Compound B | 1 | M | √ | | |
| | 2 | M | √ | | |
| | 3 | M | √ | | |
| | 4 | M | √ | | |
| | 5 | M | √ | | |
| | 6 | M | √ | | |
| | 7 | F | √ | | |
| | 8 | F | √ | | |
| | 9 | F | √ | | |
| | 10 | F | √ | | |
| | 11 | F | √ | | |
| | 12 | F | √ | | |

Animal: ICR mice.
Dose: $1/_{12}LD_{10}$/day for 5 days, i.p. (Cisplatin: 0.92 mg/kg; Carboplatin: 12.5 mg/kg; TCM: 0.068 mg/kg; Compound A: 18.2 mg/kg; Compound B: 5.56 mg/kg).
KIDNEY: Protein casts: + rare, ++ low number of protein casts within proximal tubules.

TABLE 4 (B)

HISTOPATHOLOGY STUDIES OF VARIOUS COMPOUNDS WITH DOSE OF $1/_{12}LD_{10}$

| LIVER Drug | No. | Sex | Normal | Vacuolation | Inflammation | Necrosis |
|---|---|---|---|---|---|---|
| Saline | 1 | M | √ | | | |
| | 2 | M | √ | | | |
| | 3 | M | √ | | | |
| | 4 | M | √ | | | |
| | 5 | F | √ | | | |
| | 6 | F | √ | | | |
| | 7 | F | √ | | | |
| | 8 | F | √ | | | |
| Cisplatin | 1 | M | √ | | | |
| | 2 | M | √ | | | |
| | 3 | M | √ | | | |
| | 4 | M | √ | | | |
| | 5 | F | √ | | | |
| | 6 | F | √ | | | |
| | 7 | F | √ | | | |
| | 8 | F | √ | | | |
| Carboplatin | 1 | M | √ | | | |
| | 2 | M | √ | | | |
| | 3 | M | | + | | |
| | 4 | M | | + | | |
| | 5 | M | √ | | | |
| | 6 | F | √ | | | |
| | 7 | F | √ | | | |
| | 8 | F | √ | | | |
| | 9 | F | √ | | | |
| TCM | 1 | M | √ | | | |
| | 2 | M | √ | | | |
| | 3 | M | | ++ | | |
| | 4 | M | √ | | | |
| | 5 | M | | | + | |
| | 6 | F | √ | | | |
| | 7 | F | √ | | | |
| | 8 | F | √ | | | |
| | 9 | F | | | | + |
| Compound A | 1 | M | √ | | | |
| | 2 | M | √ | | | |
| | 3 | M | √ | | | |
| | 4 | M | √ | | | |
| | 5 | M | √ | | | |
| | 6 | M | √ | | | |
| | 7 | F | √ | | | |
| | 8 | F | √ | | | |
| | 9 | F | √ | | | |
| | 10 | F | | | | + |

TABLE 4 (B)-continued

HISTOPATHOLOGY STUDIES OF VARIOUS COMPOUNDS WITH DOSE OF $1/_{12}LD_{10}$

| LIVER Drug | No. | Sex | Normal | Vacuo-lation | Inflam-mation | Necrosis |
|---|---|---|---|---|---|---|
|  | 11 | F | √ |  |  |  |
|  | 12 | F | √ |  |  |  |
| Compound B | 1 | M | √ |  |  |  |
|  | 2 | M | √ |  |  |  |
|  | 3 | M | √ |  |  |  |
|  | 4 | M | √ |  |  |  |
|  | 5 | M | √ |  |  |  |
|  | 6 | M | √ |  |  |  |
|  | 7 | F | √ |  |  |  |
|  | 8 | F | √ |  |  |  |
|  | 9 | F | √ |  |  |  |
|  | 10 | F |  |  | + |  |
|  | 11 | F | √ |  |  |  |
|  | 12 | F | √ |  |  |  |

Animal: ICR mice.
Dose: $1/_{12}LD_{10}$/day for 5 days, i.p. (Cisplatin: 0.92 mg/kg; Carboplatin: 12.5 mg/kg; TCM: 0.068 mg/kg; Compound A: 18.2 mg/kg; Compound B: 5.56 mg/kg).
LIVER: Vacuolation: + minor, ++ minimal to mild intracellular vacuolation of hepatocytes.
Inflammation: + rare, ++ several tiny foci of inflammatory cells in the liver.

SUMMARY OF THE SECOND SERIES OF EXPERIMENTS

The structures of the novel compounds A–D are as shown in FIG. 1. A summary of the significant experimental findings are as follows:

(i) All the test compounds (A,B,C,D) are more soluble in water than cisplatin and two (C,D) are more soluble than carboplatin, and hence should assist eventual formulation (FIG. 2).
(ii) All the test compounds were less toxic ($LD_{50}$, i.p., mice) when compared with cisplatin and three (A,C,D) were better than carboplatin (FIG. 3).
(iii) In vitro activity of the test compounds were significantly better than carboplatin for nearly all the cell lines examined (FIGS. 4 to 9).
The seven cell lines tested were:

| Hela | (human cervix) |
|---|---|
| HT-29 | (human colon)* |
| H-522 | (human lung) |
| L1210 | (mouse leukaemia standard) |
| CNE-1 | (human nasopharyngeal - CUHK) |
| CNE-2 | (human nasopharyngeal - CUHK) |
| CC3 | (human cervix) |

*All four compounds A–D produced in vitro antitumor activity profiles distinctly similar to that of cisplatin.

(iv) In vivo 5-day acute toxicity assessments (mice, i.p.) included daily observations, gross post-mortem and histopathology[1].
  Dose: 1/12th $LD_{10}$ * (i.p., mice, mg/kg) (approximately equal to the maximum tolerated dose, MTD, in man)[2], every 24 hr for 7 days.
  *$LD_{10}$—the dose of drug at which 10% of test animals died.

| Controls: (n = 4) | cisplatin Tests: carboplatin saline cantharidin (TCM) | compounds A & B (n = 6) |
|---|---|---|

Results: No undue toxicity was recorded with the major organs of interest, i.e., liver and kidneys, with any of the controls or test compounds. Similar non-toxicity is assumed for Compounds C and D, at this dose (Table 4).

Deduction: Test compounds A–D do not cause toxicity at the projected human MTD.

[1]Histopathology carried out by consultants, Professor R. Slocombe (validated by Dr J. Slocombe), Victorian Veterinary Pathology Services, South Yarra, Victoria, Australia.

[2]E. J. Freireich et al., (1966). Quantitative comparison of toxicity of anticancer agents in mouse, rat, hamster, dog, monkey and man. Cancer Chemotherapy Reports, 50(4), 219–244.

CONCLUSIONS

A novel series of Pt complexes which have shown advantageous physico-chemical characteristics and extremely encouraging in vitro antitumor activity against a variety of cancer cell lines have been developed.

Figure 5:
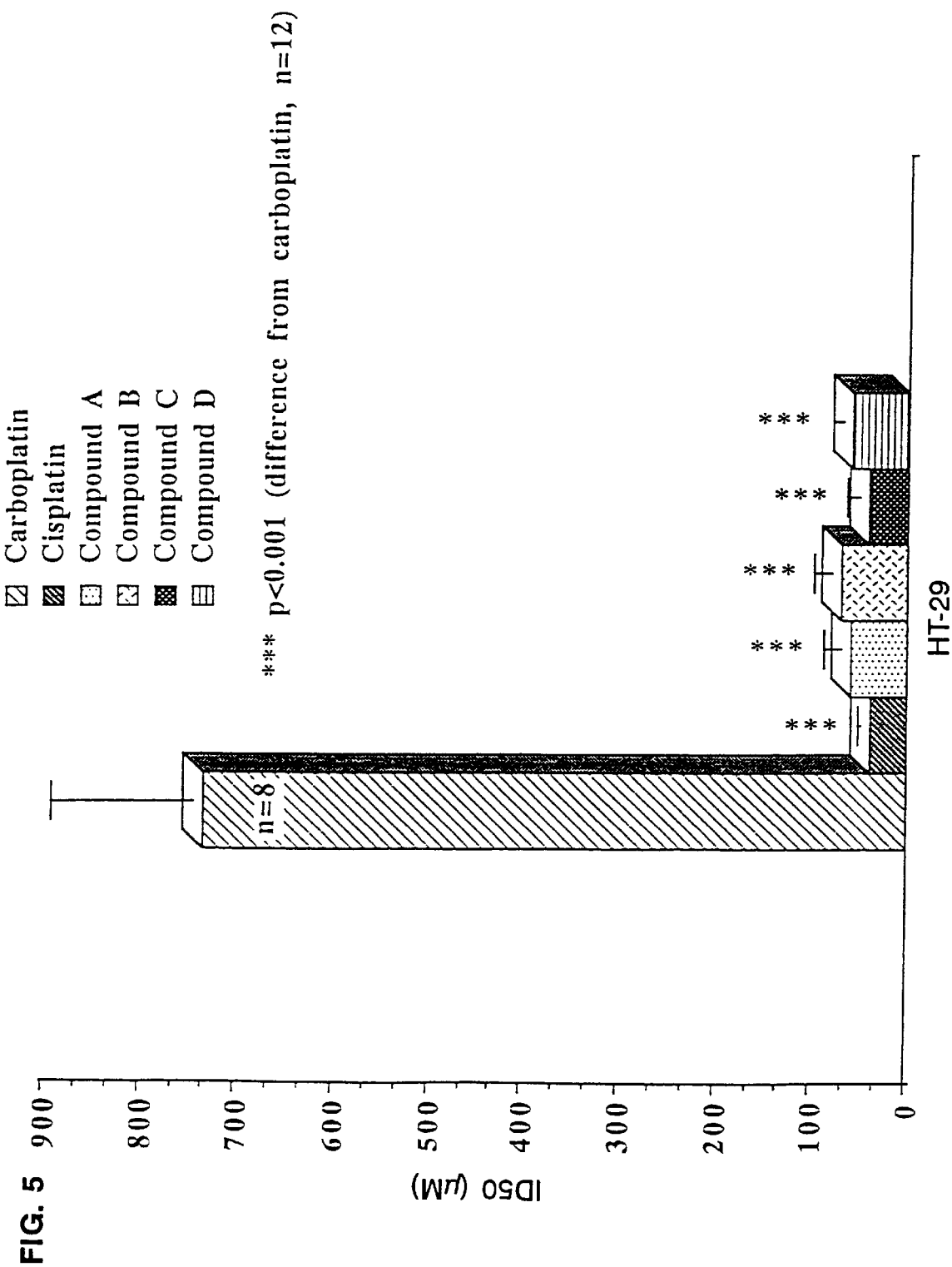
FIG. 5. ID50 (uM) of Carboplatin, Cisplatin, Compounds A, B, C and D in HT-29 cells. ***$p<0.001$ (difference from carboplatin, n=12).
Figure 6:
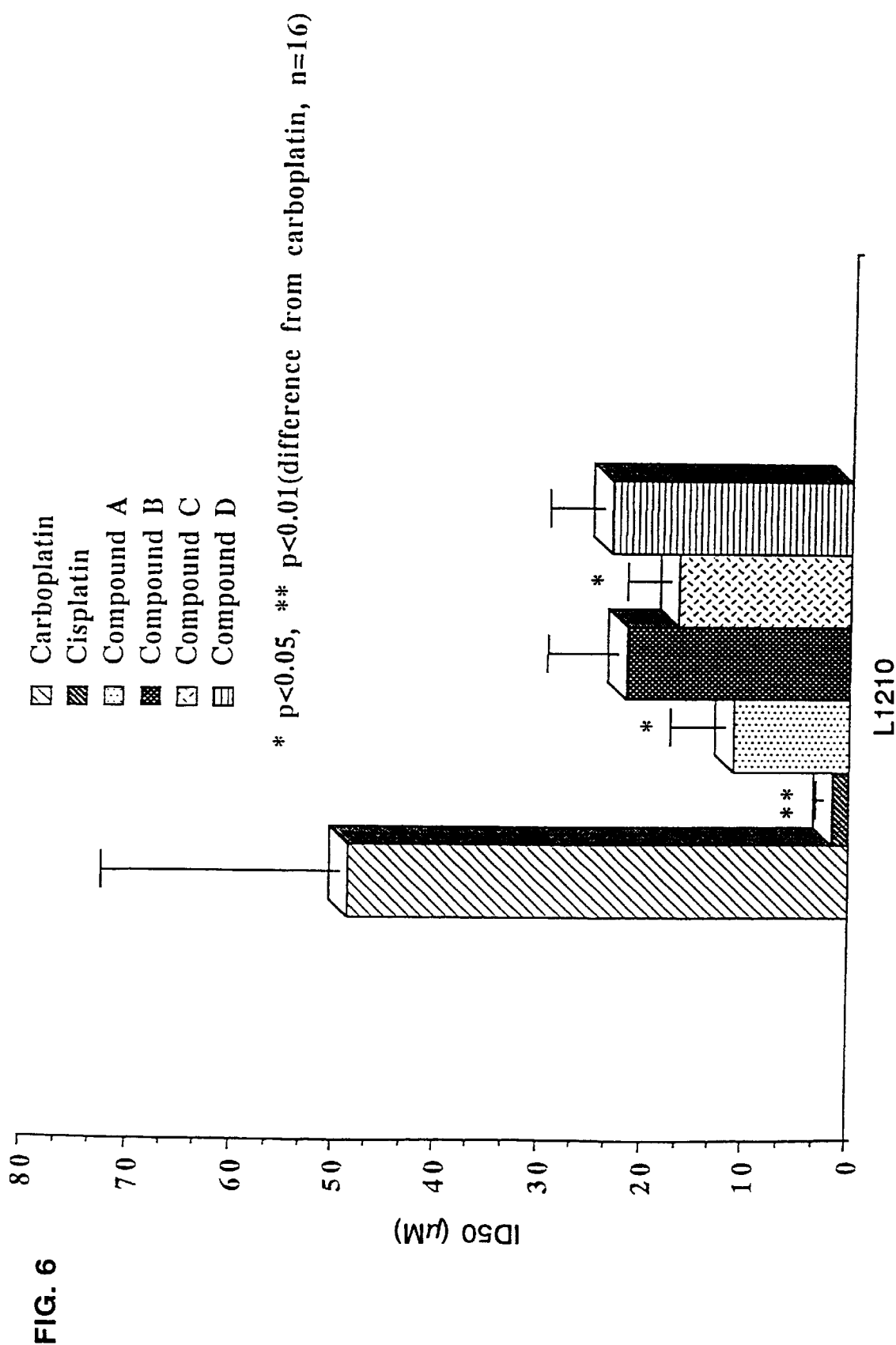
FIG. 6. ID50 (uM) of Carboplatin, Cisplatin, Compounds A, B, C and D in L1210 cells. *$p<0.05$, **$p<0.01$ (difference from carboplatin, n=16).
Figure 7:
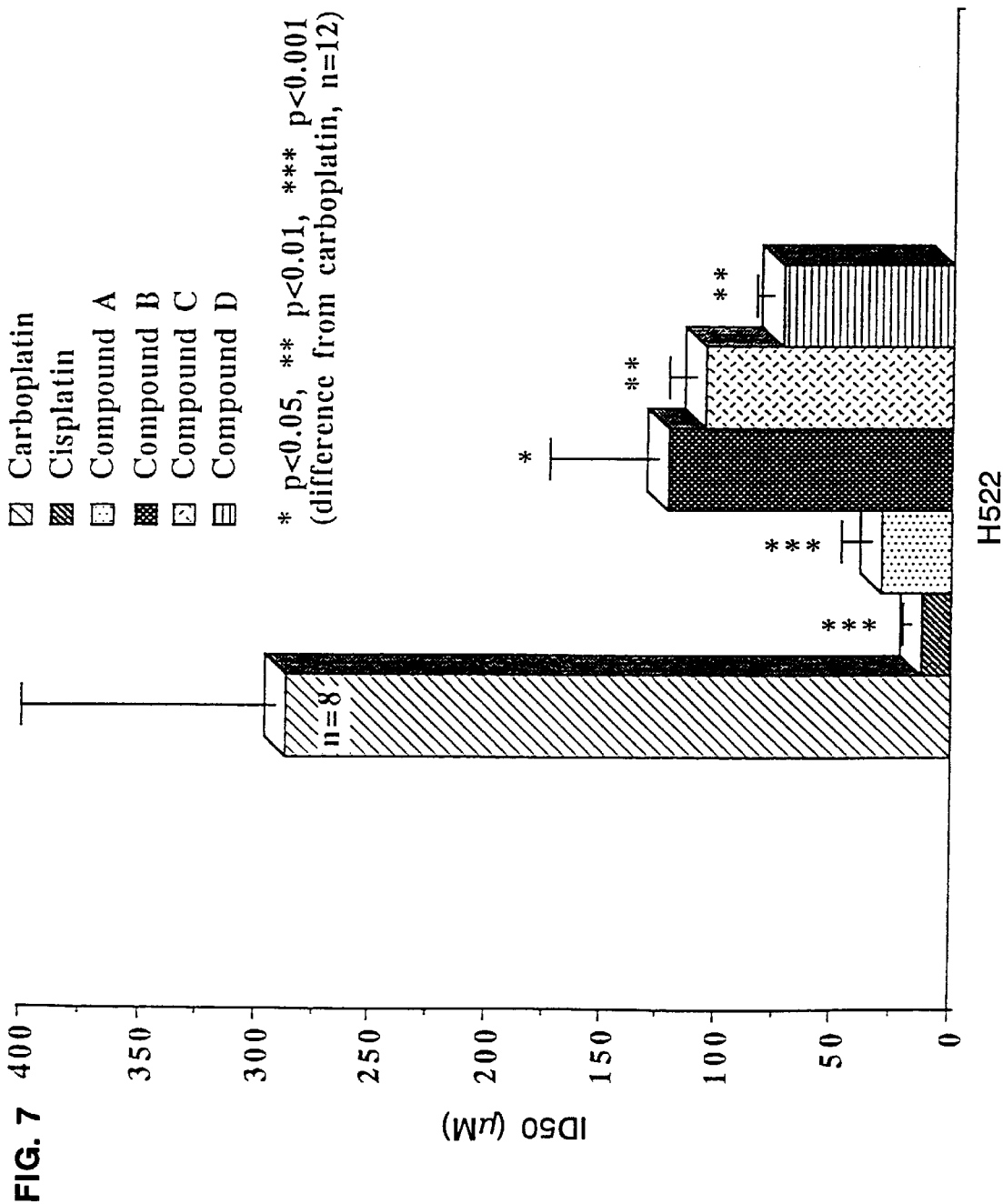
FIG. 7. ID50 (uM) of Carboplatin, Cisplatin, Compounds A, B, C and D in H522 cells. *$p<0.05$, $p<0.01$, *$p<0.001$ (difference from carboplatin, n=12).
Figure 8:
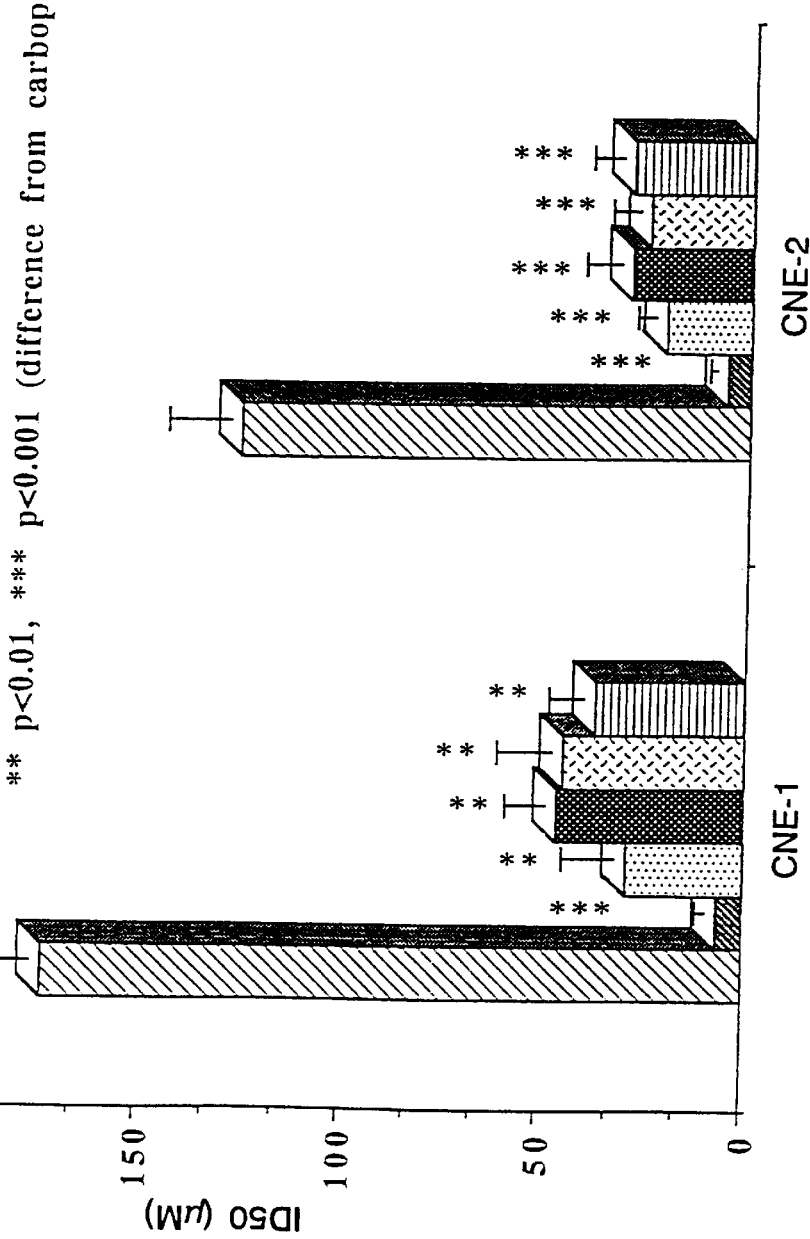
FIG. 8. ID50 (uM) of Carboplatin, Cisplatin, Compounds A, B and D in CNE-1 cells and CNE-2 cells. $p<0.01$, *$p<0.001$ (difference from carboplatin, n=16).
Figure 9:
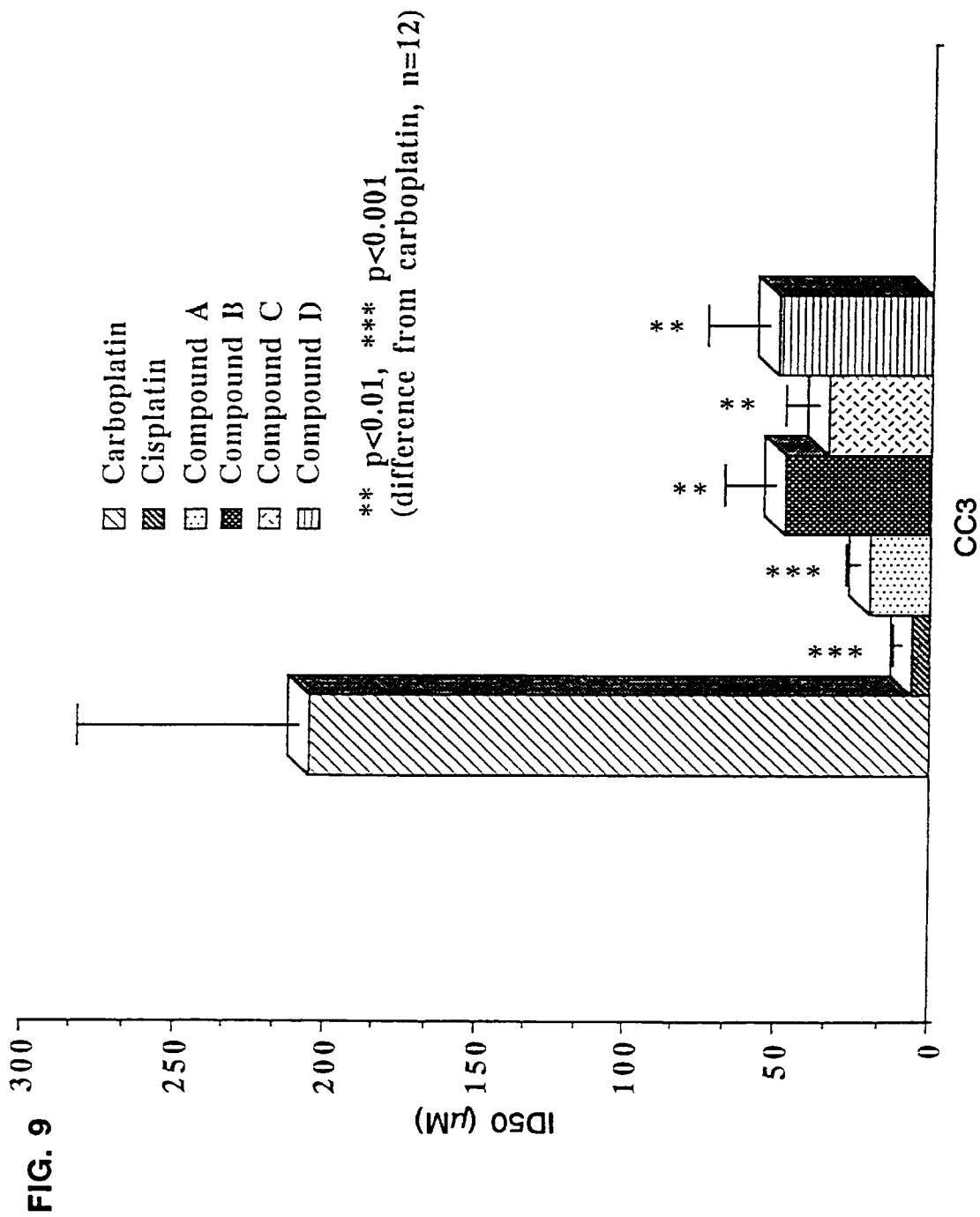
FIG. 9. ID50 (uM) of Carboplatin, Cisplatin, Compounds A, B, C and D in CC3 cells. *p<0.05, p<0.01, *p<0.001 (difference from carboplatin, n=12).

The general trend is that the novel compounds show in vitro antitumor activity significantly better than carboplatin and it is possible that the compounds are selectively more potent towards g.i. tract tumors (as shown by the high potency of the compounds towards HT-29, human colon cancer cell line, FIG. 5), due to the incorporation of cantharidin (TCM) into the novel chemical structures.

All four compounds A–D, are markedly less toxic than cisplatin ($LD_{50}$) and three (A, C, D) are less toxic than carboplatin. It is important to note that the acute toxicity studies have indicated that the novel compounds are not toxic at the estimated human maximum tolerated dose (¹⁄₁₂th $LD_{10}$ in mice)

These results suggest that the above described platinum complexes have substantial potential to be further developed as effective antitumor agents. The above findings showed a series of biologically active compounds with lower toxicity than cisplatin and carboplatin, the "golden standards".

What is claimed is:

1. A demethylcantharidin platinum complex having the following structure:

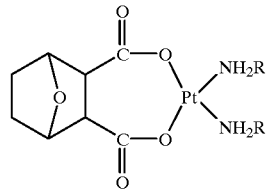

Structure I wherein R=H, C1–C10 or ring size C3–C6.

2. The demethylcantharidin platinum complex of claim 1, wherein R is H, —$CH_3$, —$C_2H_5$, —$C_3H_7$, $CH(CH_3)_2$, or cyclopropyl.

3. A demethylcantharidin platinum complex having the following structure:

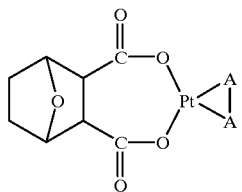

Structure II wherein —A—A is —$NH_2$—$(CH_2)_n$—$NH_2$— wherein n is 2–6;
$HO(CH_2)_m$—NH—$(CH_2)_n$—NH—$(CH_2)_mOH$ wherein m=1–5 and n=2–6; or

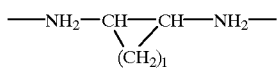

wherein l = 1–4

4. The demethylcantharidin platinum complex of claim 3, wherein n is 2–3, m is 2 or l is 4.

5. A composition comprising the demethylcantharidin platinum complex of claim 1, 2, 3 or 4 and a suitable carrier.

6. A pharmaceutical composition comprising effective amount of the demethylcantharidin platinum complex of claim 1, 2, 3 or 4 and a pharmaceutically acceptable carrier.

7. The pharmaceutical composition of claim 6 used to inhibit growth of tumor cells.

8. The pharmaceutical composition of claim 7, wherein the tumor is derived from lung, liver or colon.

9. The pharmaceutical composition of claim 7, wherein the tumor is a leukemia, lymphoma, naso-pharyngeal carcinoma or cervical tumor.

10. A method of inhibiting the growth of tumorous cells comprising contacting the cells with an amount of the demethylcantharidin platinum complex of claim 1, 2, 3 or 4 effective to inhibit the growth of said tumorous cells.

11. A method of inhibiting the growth of tumorous cells in a subject comprising administering to the subject with an amount of the demethylcantharidin platinum complex of claim 1, 2, 3 or 4 effective to inhibit the growth of said tumorous cells in the subject.

12. The method of claim 11, wherein the tumorous cells are derived from lung, liver or colon.

13. The pharmaceutical composition of claim 7, wherein the tumorous cells are leukemia cells, lymphoma cells, naso-pharyngeal carcinoma cells or cervical tumor cells.

14. A method for synthesis of demethylcantharidin platinum complex comprising:

(a) dissolving Furan and maleic anhydride in tetrahydrofuran (THF) to obtain ligand A;

(b) dissolving ligand A in ethylacetate;

(b) adding Pd-C catalyst to obtain demethylcantharidin Ligand B;

(c) adding Ligand B to a Pt (II) nitrate complex, $A_2Pt(NO_3)_2$ wherein A is $NH_2R$ and R is H, $C_1$–$C_{10}$ or ring size $C_3$–$C_6$ or

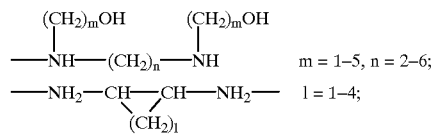

and (d) adding NaOH to the mixture from step (c) to produce a demethylcantharidin platinum complex.

15. A method of claim 14, wherein the Pt (II) nitrate complex is prepared by:

(i) converting $K_2PtCl_4$ to the iodide $K_2PtI_4$, (ii) adding amine ligand (A) or two equivalents (2A) the iodide, and (iii) adding $PtA_2I_2$ to produce $A_2Pt(NO_3)_2$.

16. A method of claim 14, wherein the Pt (II) nitrate complex is obtained directly from 2A, $K_2PtCl_4$ and $AgNO_3$.

* * * * *